(12) United States Patent
Oba et al.

(10) Patent No.: US 10,520,463 B2
(45) Date of Patent: Dec. 31, 2019

(54) GAS SENSOR

(71) Applicant: NGK Spark Plug Co., LTD., Nagoya (JP)

(72) Inventors: Takehiro Oba, Konan (JP); Shogo Nagata, Komaki (JP); Shunya Mihara, Komaki (JP)

(73) Assignee: NGK Spark Plug Co., LTD., Nagoya (JP)

( * ) Notice: Subject to any disclaimer, the term of this patent is extended or adjusted under 35 U.S.C. 154(b) by 361 days.

(21) Appl. No.: 15/481,986

(22) Filed: Apr. 7, 2017

(65) Prior Publication Data

US 2017/0307560 A1    Oct. 26, 2017

(30) Foreign Application Priority Data

Apr. 20, 2016 (JP) ................................. 2016-084805
Feb. 8, 2017 (JP) ................................. 2017-021587

(51) Int. Cl.
| G01N 27/407 | (2006.01) |
| G01N 27/30 | (2006.01) |
| G01N 27/409 | (2006.01) |
| G01N 27/406 | (2006.01) |

(52) U.S. Cl.
CPC ....... G01N 27/4073 (2013.01); G01N 27/304 (2013.01); G01N 27/409 (2013.01); G01N 27/4062 (2013.01); G01N 27/4075 (2013.01)

(58) Field of Classification Search
CPC .......... G01N 27/4073; G01N 27/4062; G01N 27/4075; G01N 27/204; G01N 27/409
See application file for complete search history.

(56) References Cited

U.S. PATENT DOCUMENTS

| 4,123,131 A | * | 10/1978 | Pearce, Jr. ......... G01N 27/4062 |
| | | | 204/428 |
| 2006/0288806 A1 | * | 12/2006 | Nelson ................ G01D 11/245 |
| | | | 73/866.5 |

FOREIGN PATENT DOCUMENTS

JP        2002-323470 A    11/2002

* cited by examiner

*Primary Examiner* — J. Christopher Ball
(74) *Attorney, Agent, or Firm* — Leason Ellis LLP

(57) ABSTRACT

An insulating separator of a gas sensor is formed to be dividable into a forward separator having a terminal disposition hole, and a rear separator having four terminal disposition holes. The insulating separator has a ventilation path formed between the forward separator and the rear separator. As a result, moisture and the like which enter the insulating separator from a forward side of the forward separator through the terminal disposition hole can be discharged outward of the insulating separator through the ventilation path. As a result, corrosion of metal terminals caused by entry of moisture can be reduced, whereby transmission of a sensor signal and application of current or voltage through the metal terminals can be appropriately implemented.

7 Claims, 17 Drawing Sheets

GAS SENSOR

This application claims the benefit of Japanese Patent Applications No. 2016-084805, filed Apr. 20, 2016 and No. 2017-021587, filed Feb. 8, 2017, all of which are incorporated herein in their entireties by reference.

FIELD OF THE INVENTION

The present invention relates to a gas sensor which includes a sensor element having a plurality of electrode terminal portions, a plurality of metal terminals electrically connected to the respective electrode terminal portions of the sensor element, a plurality of signal wires electrically connected to the respective metal terminals and forming signal paths for connecting the electrode terminal portions and external equipment, and a terminal insulation member for electrically insulating the metal terminals in contact with the respective electrode terminal portions from one another.

BACKGROUND OF THE INVENTION

A known gas sensor detects a particular component (gas targeted for detection) contained in gas to be measured. The gas sensor includes, for example, a sensor element having a plurality of electrode terminal portions, a plurality of metal terminals electrically connected to the respective electrode terminal portions of the sensor element, a plurality of signal wires electrically connected to the respective metal terminals and forming signal paths for connecting the electrode terminal portions and external equipment, and a terminal insulation member for electrically insulating the metal terminals in contact with the respective electrode terminal portions from one another. The electrode terminal portions are provided so as to output a detection signal indicative of the result of detection of detection target gas to the external equipment or to receive current or voltage from the external equipment.

The terminal insulation member provided in such a gas sensor is not limited to one formed of a single member, but a terminal insulation member composed of a plurality of members is proposed. Specifically, a proposed terminal insulation member electrically insulating the metal terminals from one another has a structure in which a first holder (40), a second holder (50), and an external connector (20) are assembled together (see Japanese Patent Application Laid-Open (kokai) No. 2002-323470).

Problem to be Solved by the Invention

However, in the case of use of the gas sensor in an environment having high humidity, moisture is apt to be generated within the gas sensor and to stagnate within the terminal insulation member, potentially causing corrosion of the metal terminals.

In view of the above problem, an object of the present invention is to provide a gas sensor which can restrain corrosion of the metal terminals caused by moisture.

SUMMARY OF THE INVENTION

Means for Solving the Problem

A gas sensor according to one aspect of the present invention comprises a sensor element, a plurality of metal terminals, a plurality of signal wires, and a terminal insulation member. Each of the metal terminals includes an element contact portion in contact with an electrode terminal portion of the sensor element and a signal-wire connection portion connected to the corresponding signal wire. The terminal insulation member is formed to be dividable into a forward insulation member having a terminal disposition hole for disposing therein at least a portion of the sensor element and at least the element contact portions of the metal terminals, and a rear insulation member having a terminal disposition hole for disposing therein at least the signal-wire connection portions of the metal terminals.

The sensor element has a plurality of electrode terminal portions. The electrode terminal portions are adapted to output a detection signal indicative of the result of detection of a target gas from the sensor element to external equipment or to input current or voltage from the external equipment to the sensor element. The metal terminals are electrically connected to the respective electrode terminal portions of the sensor element. The signal wires are electrically connected to the respective metal terminals and form signal paths for connecting the electrode terminal portions and the external equipment. The terminal insulation member electrically insulates the metal terminals in contact with the respective electrode terminal portions from one another.

In a state in which the forward insulation member and the rear insulation member are assembled together and in which the metal terminals are disposed in the terminal disposition holes, the terminal insulation member has a side ventilation path formed between the forward insulation member and the rear insulation member and extending from a side surface of the forward insulation member or from a side surface of the rear insulation member to the metal terminals.

As a result of the terminal insulation member having the side ventilation path as mentioned above, moisture and the like which enter the terminal insulation member from a forward side of the forward insulation member through the terminal disposition hole can be discharged outward of the terminal insulation member through the side ventilation path. As a result, corrosion of the metal terminals caused by entry of moisture into the terminal insulation member can be reduced, whereby transmission of a sensor signal and application of current or voltage through the metal terminals can be appropriately implemented.

Thus, the gas sensor can restrain corrosion of the metal terminals caused by moisture through employment of the terminal insulation member having the side ventilation path.

Next, in the above-mentioned gas sensor, the rear insulation member may have a plurality of the terminal disposition holes, and at least one of the terminal disposition holes may be formed so as to dispose therein one of the metal terminals and may have a sectional shape identical to a sectional shape of the signal-wire connection portion of the metal terminal in a cross section taken perpendicularly to a direction of insertion of the metal terminal.

As a result of the terminal disposition hole having such a shape, in inserting the metal terminal into the terminal disposition hole, the relative position of the metal terminal (particularly, the signal-wire connection portion) in relation to the terminal disposition hole (in other words, the relative position in the direction of rotation about the direction of insertion) can be determined on the basis of the sectional shape. Accordingly, the relative position of the metal terminal in relation to the terminal disposition hole can be easily determined, thereby facilitating the work of inserting the metal terminal into the terminal disposition hole.

Examples of the sectional shapes of the terminal disposition hole and the signal-wire connection portion include a circle and a regular polygon.

For example, in the case where the sectional shape is a circle, despite a change in the relative position of the signal-wire connection portion in the direction of rotation about the direction of insertion of the signal-wire connection portion in relation to the terminal disposition hole, the relative position suited for the work of insertion can be maintained at all times. As a result, since the work of insertion can be easily performed without need to strictly adjust the relative position (the relative position in the direction of rotation) of the signal-wire connection portion in relation to the terminal disposition hole, complication of the work of insertion can be mitigated.

In the case where the sectional shape is a regular polygon, the relative position of the signal-wire connection portion in the direction of rotation about the direction of insertion of the signal-wire connection portion in relation to the terminal disposition hole can be determined on the basis of the sectional shape of the terminal disposition hole and the sectional shape of the signal-wire connection portion. Accordingly, the relative position of the metal terminal in relation to the terminal disposition hole can be easily determined, thereby facilitating the work of inserting the metal terminal into the terminal disposition hole.

Notably, the concept "circle" with respect to the sectional shape of the signal-wire connection portion encompasses not only a breakless complete circle but also a circle having a break(s). Similarly, the concept "regular polygon" encompasses not only a breakless complete regular polygon but also a regular polygon having a break(s).

Next, in the above-mentioned gas sensor, the rear insulation member may have at least one terminal disposition hole formed so as to dispose therein a plurality of the metal terminals.

Since the rear insulation member having such a structure can have such a gap region in the terminal disposition hole as not to be occupied by the metal terminals, the terminal insulation member easily discharges moisture generated therein outward through the gap region of the terminal disposition hole.

Therefore, the gas sensor equipped with the terminal insulation member having such a rear insulation member can further restrain corrosion of the metal terminals caused by moisture.

Next, in the above-mentioned gas sensor, the terminal insulation member may have an inter-terminal ventilation path in the form of a space extending to at least two of the metal terminals.

As a result of the terminal insulation member having the inter-terminal ventilation path in addition to the side ventilation path extending from a side to the metal terminals as mentioned above, ventilation within the terminal insulation member is further improved, thereby facilitating discharge of moisture.

Therefore, the gas sensor equipped with the terminal insulation member having such an inter-terminal ventilation path can further restrain corrosion of the metal terminals caused by moisture.

Next, in the above-mentioned gas sensor equipped with the terminal insulation member having the inter-terminal ventilation path, the inter-terminal ventilation path may be formed in the form of a space extending to all the metal terminals.

As a result of the inter-terminal ventilation path having such a structure, ventilation within the terminal insulation member is further improved, whereby stagnation of moisture around the metal terminals can be restrained.

Next, in the above-mentioned gas sensor, the metal terminal may comprise a forward terminal member having the element contact portion, and a rear terminal member having the signal-wire connection portion. The forward terminal member has a female connection portion. The rear terminal member has a male connection portion connected to the female connection portion. The forward terminal member and the rear terminal member electrically connect the corresponding electrode terminal portion and the corresponding signal wire as a result of the male connection portion and the female connection portion being connected together.

Since, at a stage prior to connecting the forward terminal member and the rear terminal member together, the metal terminal having such a structure allows the work of bringing the element contact portion (the forward terminal member) into contact with the electrode terminal portion and the work of connecting the signal-wire connection portion (the rear terminal member) to the signal wire to be performed separately, working is possible even in a state in which the sensor element and the signal wire are separated from each other. By connecting together the forward terminal member in contact with the electrode terminal portion and the rear terminal member connected to the signal wire, the electrode terminal portion and the signal wire can be electrically connected.

Use of the metal terminal having the forward terminal member and the rear terminal member as mentioned above can mitigate complication of the work of electrically connecting the electrode terminal portion and the signal wire.

Next, in the above-mentioned gas sensor equipped with the metal terminals each having the forward terminal member and the rear terminal member, the metal terminal may have a weld zone for joining the forward terminal member and the rear terminal member together.

As a result of the metal terminal having the weld zone, a physical separation between the forward terminal member and the rear terminal member can be restrained, whereby the electrical connection between the forward terminal member and the rear terminal member can be maintained in a good condition.

Next, in the above-mentioned gas sensor, the rear insulation member may have a ventilation through hole extending therethrough between forward end side and rear end side of the rear insulation member.

As a result of the rear insulation member having the ventilation through hole as mentioned above, since moisture existing within the terminal insulation member can be discharged outward through the ventilation through hole, ventilation is further improved.

Effect of the Invention

The gas sensor of the present invention can restrain corrosion of the metal terminals caused by moisture through employment of the terminal insulation member having the side ventilation path.

BRIEF DESCRIPTION OF THE DRAWINGS

These and other features and advantages of the present invention will become more readily appreciated when considered in connection with the following detailed description and appended drawings, wherein like designations denote like elements in the various views, and wherein.

DETAILED DESCRIPTION OF THE INVENTION

Embodiments of the present invention will next be described with reference to the drawings.

The present invention is not limited to the following embodiments, but can be embodied in various modes without departing from the technical scope of the present invention.

[1. First Embodiment]
[1-1. Overall Configuration]

A first embodiment will be described while referring to an oxygen sensor (hereinafter, may be called a gas sensor 1) which is attached to an exhaust pipe of an internal combustion engine with a forward end portion thereof protruding into the exhaust pipe, for detecting oxygen contained in exhaust gas. The gas sensor 1 is attached to, for example, an exhaust pipe of a vehicle such as an automobile or a motorcycle.

First, the configuration of the gas sensor 1 of the present embodiment will be described with reference to FIG. 1.

Figure 1:
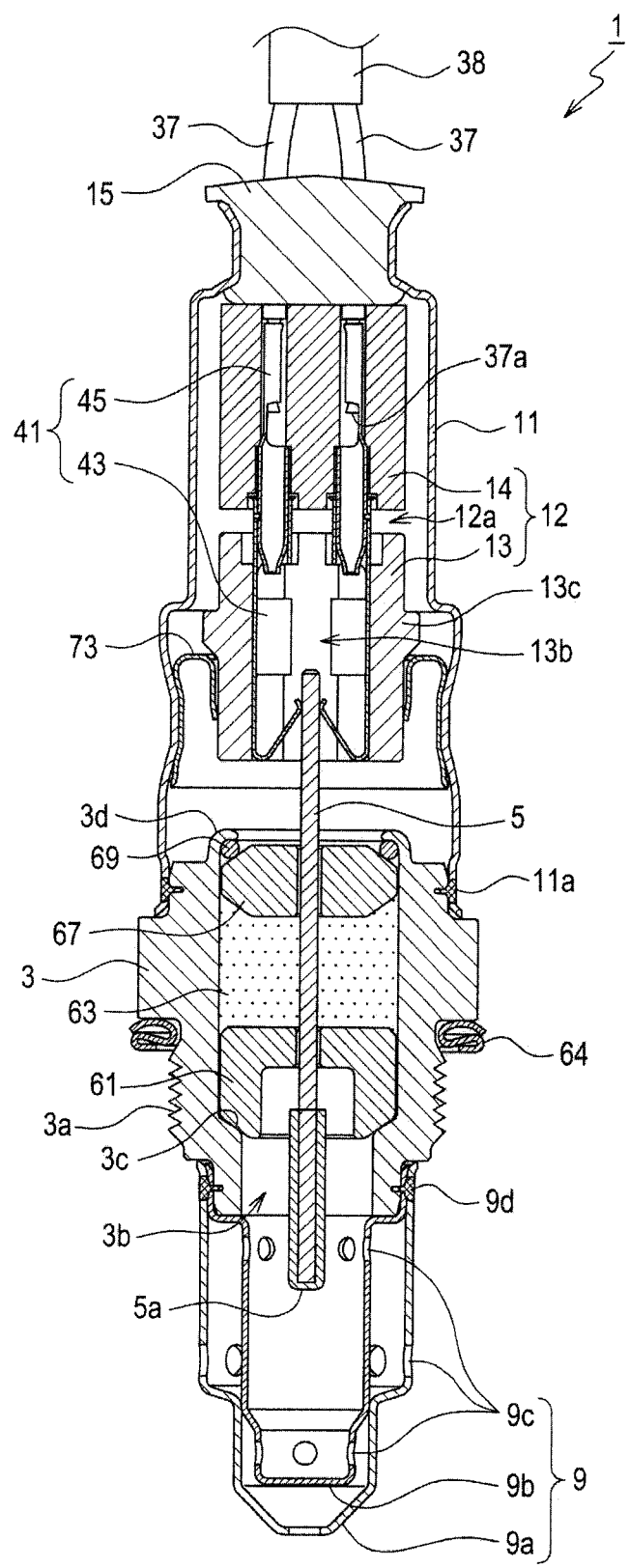
FIG. 1 is a sectional view showing the overall configuration of a gas sensor according to an embodiment of the present invention.

In FIG. 1, a lower side of the drawing corresponds to a forward side of the gas sensor, and an upper side corresponds to a rear side of the gas sensor.

The gas sensor 1 includes a tubular metallic shell 3 to be fixed to an exhaust pipe (not shown); a plate-like detection element 5 inserted through the metallic shell 3 and extending in the axial direction (the longitudinal direction of the gas sensor 1, or the vertical direction in FIG. 1); an element protector 9 disposed on the forward side (the lower side in FIG. 1) of the metallic shell 3 and covering a forward end portion of the detection element 5; a sleeve 11 attached to a rear end portion (an upper end portion in FIG. 1) of the metallic shell 3 through a weld zone 11a and radially surrounding the detection element 5; an insulating separator 12 disposed inside the sleeve 11 and accommodating a rear end portion of the detection element 5; a plug member 15 plugging a rear end portion of the sleeve 11; a plurality of (four in the present embodiment) metal terminals 41; and a plurality of (four in the present embodiment) lead wires 37.

The detection element 5 has a detecting section 19 formed at its forward end portion directed toward an object of measurement (exhaust gas, etc.,) and covered with a protection layer 5a, and electrode terminal portions (first to fourth electrode terminal portions) 31, 32, 34, and 35 formed on the outer surface of its rear end portion; i.e., on the front and back surfaces of the rear end portion; specifically, on a first plate surface 21 and a second plate surface 23 of the rear end portion.

The detection element 5 is fixed inside the metallic shell 3 such that the forward detecting section 19 protrudes from the forward end of the metallic shell 3 fixed to the exhaust pipe, whereas the rear electrode terminal portions 31, 32, 34, and 35 protrude from the rear end of the metallic shell 3.

The metal terminals 41 are connected to the electrode terminal portions 31, 32, 34, and 35, respectively. Specifically, a plurality of the metal terminals 41 are disposed inside the insulating separator 12 between the detection element 5 and the insulating separator 12, thereby being electrically connected to the electrode terminal portions 31, 32, 34, and 35, respectively, of the detection element 5. Each of the metal terminals 41 is composed of a forward terminal member 43 and a rear terminal member 45.

A plurality of the metal terminals 41 are electrically connected to a plurality of the lead wires 37 (specifically cores 37a of the lead wires 37), respectively, which extend from external equipment (not shown) and are disposed inside the gas sensor 1.

The structure of the metal terminal 41 will be described later in detail.

The metal terminals 41 and the lead wires 37 form current paths through which electric current flows between the detection element 5 (specifically, the electrode terminal portions 31, 32, 34, and 35) and external equipment connected to the lead wires 37. A plurality of the lead wires 37 are bundled in a tube member 38. FIG. 1 shows only two of the lead wires 37.

Figure 2:
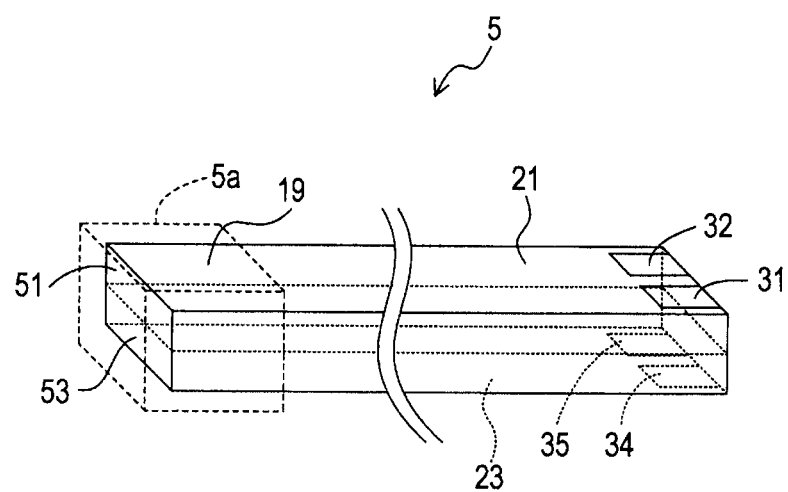
FIG. 2 is a perspective view showing the schematic structure of a detection element.

FIG. 2 is a perspective view showing a schematic structure of the detection element 5. FIG. 2 shows the detection element 5 with its axially intermediate portion eliminated.

As shown in FIG. 2, the detection element 5 is a rectangular parallelepiped laminate of a plate-like element body 51 extending in the axial direction (the horizontal direction in FIG. 2) and a plate-like heater 53 extending in the axial direction and has a rectangular section taken perpendicularly to the axial direction. In FIG. 2, the protection layer 5a is indicated by the dotted line.

Since the detection element 5 of the gas sensor 1 is a publicly known element, a detailed description of its internal structure, etc., is omitted, but its schematic structure is as follows.

First, the element body 51 includes, for example, an oxygen concentration cell formed by forming porous electrodes on respective opposite sides of a solid electrolyte substrate, and a spacer for forming a hollow reference gas chamber. The solid electrolyte substrate is formed of, for example, zirconia which contains yttria as a stabilizer in solid solution, and the porous electrodes are formed primarily of Pt, for example. The spacer used to form the reference gas chamber is formed primarily of alumina, and one of the two porous electrodes of the oxygen concentration cell is exposed to the interior of the hollow reference gas chamber. The spacer is formed such that the reference gas chamber is located at least at a forward end portion of the element body 51, and has a gas passage for introducing reference gas (air, for example) from outside into the reference gas chamber. A region of the element body 51 where the porous electrodes and the reference gas chamber are formed corresponds to the detecting section 19.

Meanwhile, the heater 53 is formed such that a heat generation resistor pattern formed primarily of Pt is sandwiched between insulating substrates formed primarily of alumina. The element body 51 and the heater 53 are joined together through a ceramic layer (zirconia ceramic or alumina ceramic, for example).

The detection element 5 has the protection layer 5a (not shown in FIG. 2) formed of porous ceramic on its forward end portion; at least, on the surface of the electrode to be exposed to an object of measurement (exhaust gas in the present embodiment), for the purpose of prevention of poisoning. As shown in FIG. 1, in the detection element 5 of the present embodiment, the protection layer 5a covers the entire surface of a forward end portion thereof which includes the surface of the porous electrode to be exposed to exhaust gas.

In the detection element 5 having such a structure, as shown in FIG. 2, two electrode terminal portions 31 and 32 are formed on a rear end portion (a right end portion in FIG. 2) of the first plate surface 21, and two electrode terminal portions 34 and 35 are formed on a rear end portion of the second plate surface 23. The electrode terminal portions 31 and 32 are formed on the element body 51 and are electrically connected to a pair of the porous electrodes, respectively, of the oxygen concentration cell. The electrode terminal portions 34 and 35 are formed on the heater 53 and are connected to opposite ends, respectively, of the heat generation resistor pattern through via conductors (not shown) extending through the heater in the heater thickness direction.

Referring back to FIG. 1, the metallic shell 3 is a tubular member having a threaded portion 3a formed on its outer surface for fixing the same to the exhaust pipe, and having a central through hole 3b extending therethrough in the axial direction. The metallic shell 3 has a ledge portion 3c protruding radially inward from the wall of the through hole 3b. The metallic shell 3 is formed of a metal material (e.g., stainless steel).

The through hole 3b of the metallic shell 3 accommodates an annular holder 61 (an annular ceramic holder 61) formed of an insulating material (e.g., alumina) and disposed in such a manner as to radially surround the detection element 5, an annular charged powder layer 63 (a talc ring 63), and an annular sleeve 67 (an annular ceramic sleeve 67) formed of an insulating material (e.g., alumina), which are stacked in this order from the forward side.

A crimp packing 69 is disposed between the ceramic sleeve 67 and a rear end portion 3d of the metallic shell 3.

The rear end portion 3d of the metallic shell 3 is crimped so as to press forward the ceramic sleeve 67 through the crimp packing 69.

An annular gasket 64 is disposed rearward of the threaded portion 3a around the outer circumference of the metallic shell 3. The gasket 64 restrains leakage of gas from the gap between the gas sensor 1 and a sensor attachment region (exhaust pipe).

The element protector 9 is a tubular member attached to the outer circumference of a forward end portion of the metallic shell 3 through a weld zone 9d in such a manner as to cover a protruding portion of the detection element 5. The element protector 9 is formed of a heat resistant material (e.g., SUS310). The element protector 9 has a dual structure consisting of an outer protector 9a and an inner protector 9b. The outer protector 9a and the inner protector 9b have a plurality of holes 9c formed in the side wall or in a forward end portion for allowing passage of gas therethrough.

The insulating separator 12 is formed to be dividable into a forward separator 13 and a rear separator 14.

The forward separator 13 is a tubular member formed of an insulating material (e.g., alumina) and is held to the inner wall of the sleeve 11 by a tubular metal holding member 73 disposed within the sleeve 11. The forward separator 13 has a terminal disposition hole 13b extending therethrough in the axial direction. The terminal disposition hole 13b accommodates a rear end portion (electrode terminal portions 31, 32, 34, and 35) of the detection element 5, and forward portions (specifically, the forward terminal members 43) of a plurality of the metal terminals 41 to be electrically connected to the electrode terminal portions 31, 32, 34, and 35, respectively. The forward separator 13 has an annular collar portion 13c protruding outward from the outer surface thereof. The axial position of the forward separator 13 can be fixed within the sleeve 11 by means of the collar portion 13c coming into contact with the metal holding member 73.

The rear separator 14 is a tubular member formed of an insulating material (e.g., alumina) and is disposed forward of the plug member 15 within the sleeve 11. The rear separator 14 has a plurality of terminal disposition holes 14b extending therethrough in the axial direction. The rear separator 14 accommodates rear portions (specifically, the rear terminal members 45) of the metal terminals 41 in a plurality of the terminal disposition holes 14b, respectively.

The structure of the insulating separator 12 (the forward separator 13 and the rear separator 14) will be described in detail later.

The plug member 15 is a grommet formed of a flexible material (e.g., fluororesin). The plug member 15 is disposed in a rear-end opening portion of the sleeve 11 and is fixed to the sleeve 11 by means of the sleeve 11 being crimped inward from outside. The plug member 15 has a plurality of through holes (not shown) formed therein for allowing a plurality of the lead wires 37 to be inserted through the through holes, respectively.

A plurality of the lead wires 37 are connected (by crimping) to rear end portions of the metal terminals 41, respectively, are inserted respectively through the through holes extending through the plug member 15, and extend toward the external equipment.

[1-2. Metal Terminal]

Next, the metal terminal 41 will be described.

As mentioned above, the metal terminal 41 is composed of the forward terminal member 43 and the rear terminal member 45. That is, the metal terminal 41 is not a single member, but is composed of the forward terminal member 43 and the rear terminal member 45.

Figure 3:
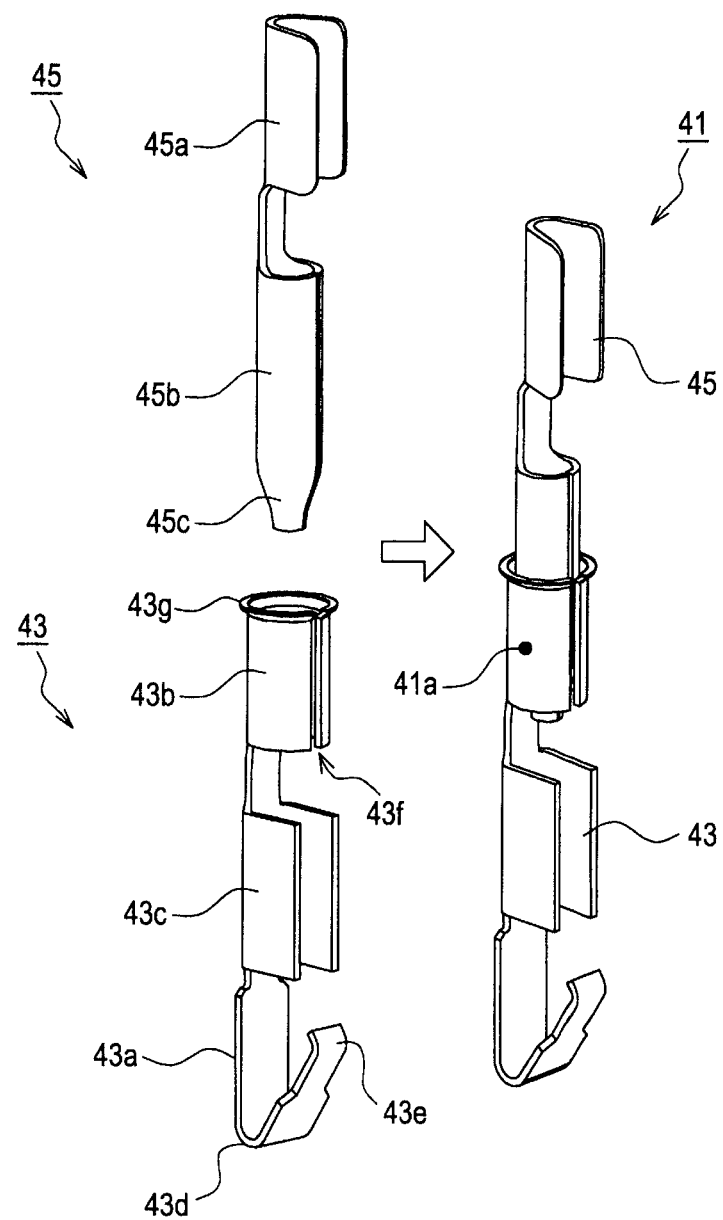
FIG. 3 is an explanatory view showing the structure of a metal terminal composed of a forward terminal member and a rear terminal member.

FIG. 3 is an explanatory view showing the structure of the metal terminal 41 composed of the forward terminal member 43 and the rear terminal member 45.

The forward terminal member 43 is formed of a metal material which can maintain elasticity (spring elasticity) even in repeated exposure to high temperature; for example, an alloy material which predominantly contains Ni (NCF718 or the like). The forward terminal member 43 is formed by bending an elongated sheet-like metal material and includes a body portion 43a, a female connection portion 43b, extension portions 43c, a bend portion 43d, and an element contact portion 43e.

The body portion 43a has an elongated plate-like shape extending in the axial direction.

The female connection portion 43b is located rearward of the body portion 43a, has a tubular shape, and has a circular section taken perpendicularly to the axial direction. The female connection portion 43b has a slit 43f for allowing a change of the inside diameter of the tubular shape in response to elastic deformation. Thus, the sectional shape of the female connection portion 43b is strictly a circle with a break. The female connection portion 43b also has a rear-end diameter-expanding portion 43g. The diameter-expanding portion 43g is shaped such that the diameter increases rearward.

The extension portions 43c extend from the sides of the body portion 43a in a direction perpendicular to the plate surface of the body portion 43a. Two extension portions 43c extend from the body portion 43a. The extension portions 43c improve the strength of the body portion 43a.

The bend portion 43d is bent in a direction perpendicular to the plate surface of the body portion 43a at the forward end of the body portion 43a and connects the body portion 43a and the element contact portion 43e.

The element contact portion 43e is connected to the body portion 43a through the bend portion 43d, and the size of the gap between the body portion 43a and the element contact portion 43e can be changed through elastic deformation of the bend portion 43d.

The forward terminal member 43 having such a structure can maintain contact between the element contact portion 43e and the detection element 5 through elastic deformation of the bend portion 43d resulting from contact of the element contact portion 43e with the detection element 5 (specifically, the electrode terminal portion 31, 32, 34, or 35).

Next, the rear terminal member 45 is formed of a metal material, such as a stainless steel alloy (SUS304), smaller in "0.2% yield strength" than a metal material used to form the forward terminal member 43. The rear terminal member 45 is formed by bending an elongated sheet-like metal material and includes a signal-wire connection portion 45a and a male connection portion 45b. Notably, "0.2% yield strength" is obtained in accordance with JIS Z2241.

The signal-wire connection portion 45a is deformed, by bending, into such a tubular shape as to surround the core 37a of the lead wire 37 (see FIG. 1). The signal-wire connection portion 45a is crimped radially inward while surrounding the core 37a of the lead wire 37, thereby being mechanically and electrically connected to the core 37a of the lead wire 37.

The male connection portion 45b is located forward of the signal-wire connection portion 45a, has a tubular shape, and has a circular section taken perpendicularly to the axial direction. The male connection portion 45b has such an outside diameter as to allow insertion thereof into the female connection portion 43b. The male connection portion 45b has a forward-end diameter-reducing portion 45c. The diameter-reducing portion 45c is shaped such that the diameter reduces forward.

The rear terminal member 45 having such a structure is electrically connected to external equipment through the lead wire 37 as a result of the signal-wire connection portion 45a being electrically connected to the core 37a of the lead wire 37.

As shown at the right of FIG. 3, the metal terminal 41 is configured such that the forward terminal member 43 and the rear terminal member 45 are connected together. More specifically, the metal terminal 41 composed of the forward terminal member 43 and the rear terminal member 45 is formed through connection of the male connection portion 45b and the female connection portion 43b.

The metal terminal 41 has a weld zone 41a for joining the male connection portion 45b and the female connection portion 43b together.

If the weld zone 41a is not provided, the male connection portion 45b and the female connection portion 43b can be disconnected from each other. However, as a result of the metal terminal 41 having the weld zone 41a, a physical separation between the forward terminal member 43 and the rear terminal member 45 can be restrained, whereby an electrical connection between the forward terminal member 43 and the rear terminal member 45 can be maintained in a good condition.

The metal terminal 41 having such a structure is configured such that the element contact portion 43e of the forward terminal member 43 is electrically connected to the detection element 5 (specifically, the electrode terminal portion 31, 32, 34, or 35) while the signal-wire connection portion 45a of the rear terminal member 45 is electrically connected to external equipment through the lead wire 37.

The forward terminal member 43 is formed of an alloy material which predominantly contains Ni, and the rear terminal member 45 is formed of a stainless steel alloy. An alloy material which predominantly contains Ni is superior in heat resistance to and greater in "0.2% yield strength" than a stainless steel alloy. That is, the forward terminal member 43 is formed of a material superior in heat resistance to and larger in elastic deformation region than a material used to form the rear terminal member 45.

[1-3. Insulating Separator]

Next, the insulating separator 12 will be described.

As mentioned above, the insulating separator 12 can be divided into the forward separator 13 and the rear separator 14.

Figure 4:
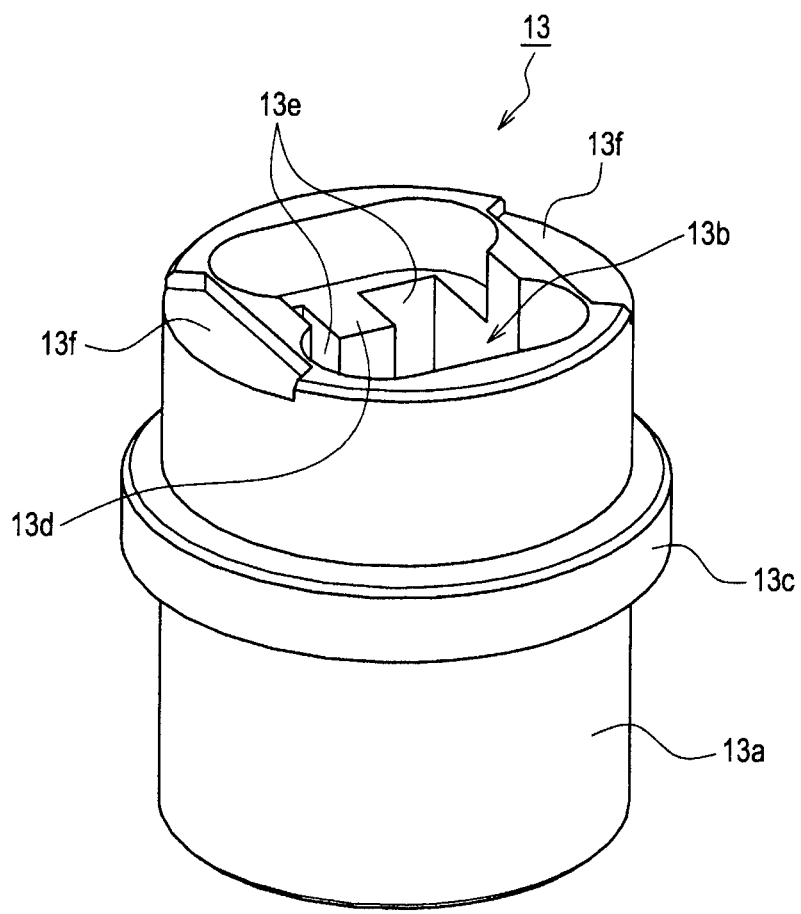
FIG. 4 is a perspective view of a forward separator as viewed from obliquely above on the rear side.
Figure 5:
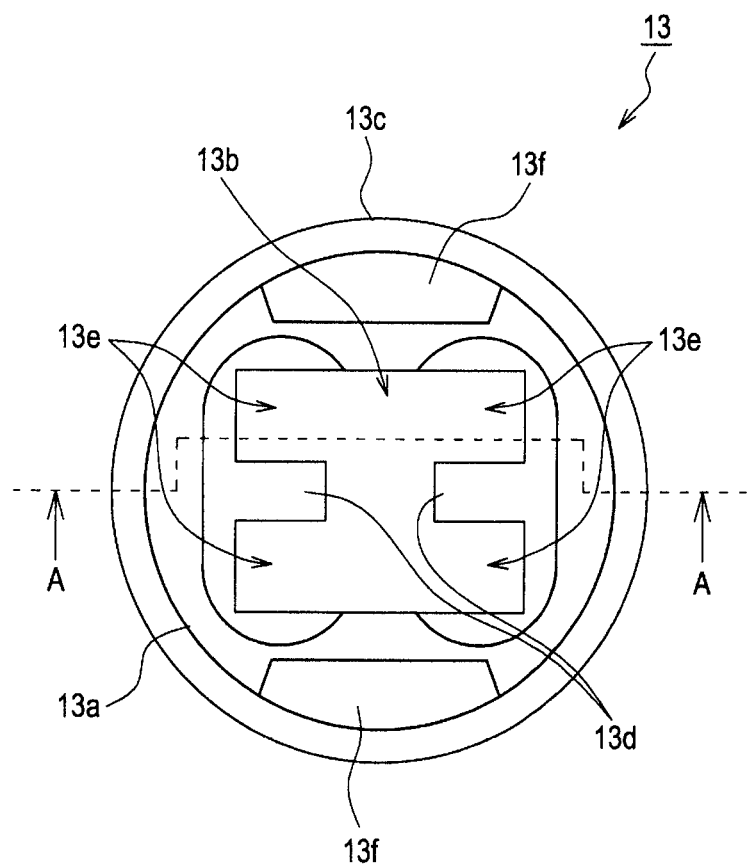
FIG. 5 is an exterior view of the forward separator as viewed from the rear side.
Figure 6:
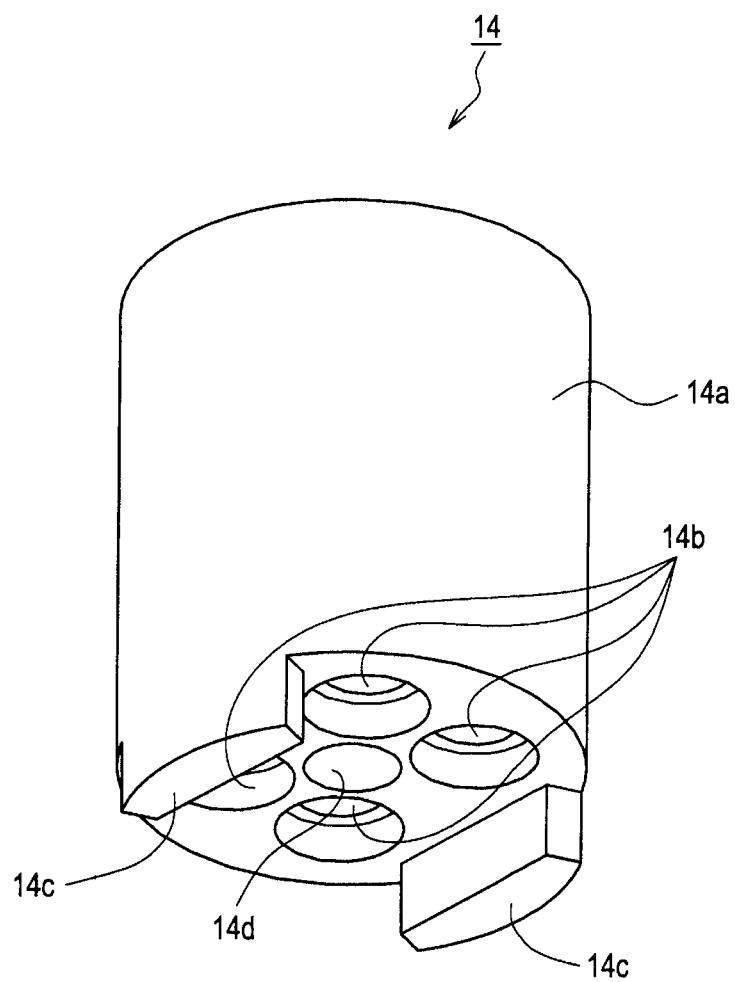
FIG. 6 is a perspective view of a rear separator as viewed from obliquely underneath on the forward side.
Figure 7:
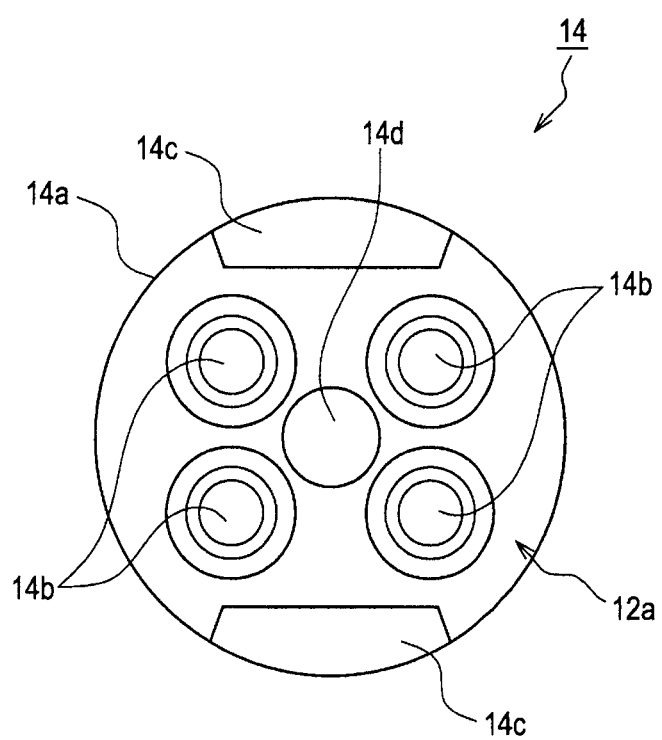
FIG. 7 is an exterior view of the rear separator as viewed from the forward side.

FIG. 4 is a perspective view of the forward separator 13 as viewed from obliquely above on the rear side, and FIG. 5 is an exterior view of the forward separator 13 as viewed from the rear side. FIG. 6 is a perspective view of the rear separator 14 as viewed from obliquely underneath on the forward side, and FIG. 7 is an exterior view of the rear separator 14 as viewed from the forward side. In the sectional view of the gas sensor 1 in FIG. 1, the section of the insulating separator 12 is taken along line A-A of FIG. 5.

First, the forward separator 13 will be described.

As mentioned above, the forward separator 13 is a tubular member formed of an insulating material (e.g., alumina). As shown in FIGS. 4 and 5, the forward separator 13 includes a tubular separator body portion 13a and a collar portion 13c.

The separator body portion 13a has a terminal disposition hole 13b extending therethrough in the axial direction. The separator body portion 13a has two partitions 13d protruding inward from the wall surface of the terminal disposition hole 13b and extending in the axial direction. Each partition 13d is formed between two terminal disposition regions 13e and prevents contact (electrical short circuit) between two metal terminals 41 (more specifically, two forward terminal members 43) disposed in the two adjacent terminal disposition regions 13e, respectively. The two partitions 13d are formed on the wall surface of the terminal disposition hole 13b in such a manner as to face each other.

That is, the forward separator 13 has four terminal disposition regions 13e in the terminal disposition hole 13b for allowing four metal terminals 41 (four forward terminal members 43) to be disposed therein in a mutually electrically insulated condition.

The terminal disposition hole 13b has such a size as to accommodate a rear end portion of the detection element 5 in a region between the two partitions 13d while the metal terminals 41 (the forward terminal members 43) are disposed in the four terminal disposition regions 13e, respectively.

That is, the forward separator 13 accommodates the four metal terminals 41 (the four forward terminal members 43) and a rear end portion of the detection element 5 in the terminal disposition hole 13b and establishes electrical connection between the four metal terminals 41 (the four forward terminal members 43) and the electrode terminal portions 31, 32, 34, and 35, respectively, of the detection element 5.

The collar portion 13c protrudes outward from the outer surface of the separator body portion 13a and is formed annularly along the outer surface of the separator body portion 13a.

The forward separator 13 also has two recesses 13f formed at the rear end of the separator body portion 13a.

Next, the rear separator 14 will be described.

As mentioned above, the rear separator 14 is a tubular member formed of an insulating material (e.g., alumina). As shown in FIGS. 6 and 7, the rear separator 14 includes a tubular separator body portion 14a and protrusions 14c.

The separator body portion 14a has a plurality of (four in the present embodiment) the terminal disposition holes 14b extending therethrough in the axial direction. Each of the terminal disposition holes 14b has a circular section taken perpendicularly to the axial direction and has such a size as to accommodate a rear end portion (the rear terminal member 45) of the metal terminal 41. In the rear separator 14, a single metal terminal 41 is disposed in a single terminal disposition hole 14b, thereby preventing contact (electrical short circuit) between the metal terminals 41 (more specifically, the rear terminal members 45).

The separator body portion 14a also has a ventilation through hole 14d extending therethrough in the axial direction. By virtue of the rear separator 14 having the ventilation through hole 14d, moisture or the like existing between the forward separator 13 and the rear separator 14 can be discharged outward through the ventilation through hole 14d. The plug member 15 has a ventilation hole (not shown in FIG. 1) communicating with the ventilation through hole 14d and with the outside.

The protrusions 14c protrude forward from the forward end of the separator body portion 14a. The two protrusions 14c are formed at the forward end of the separator body portion 14a. The positions of the two protrusions 14c protruding from the separator body portion 14a correspond to the positions of the two recesses 13f of the forward separator 13 (separator body portion 13a).

Figure 8:
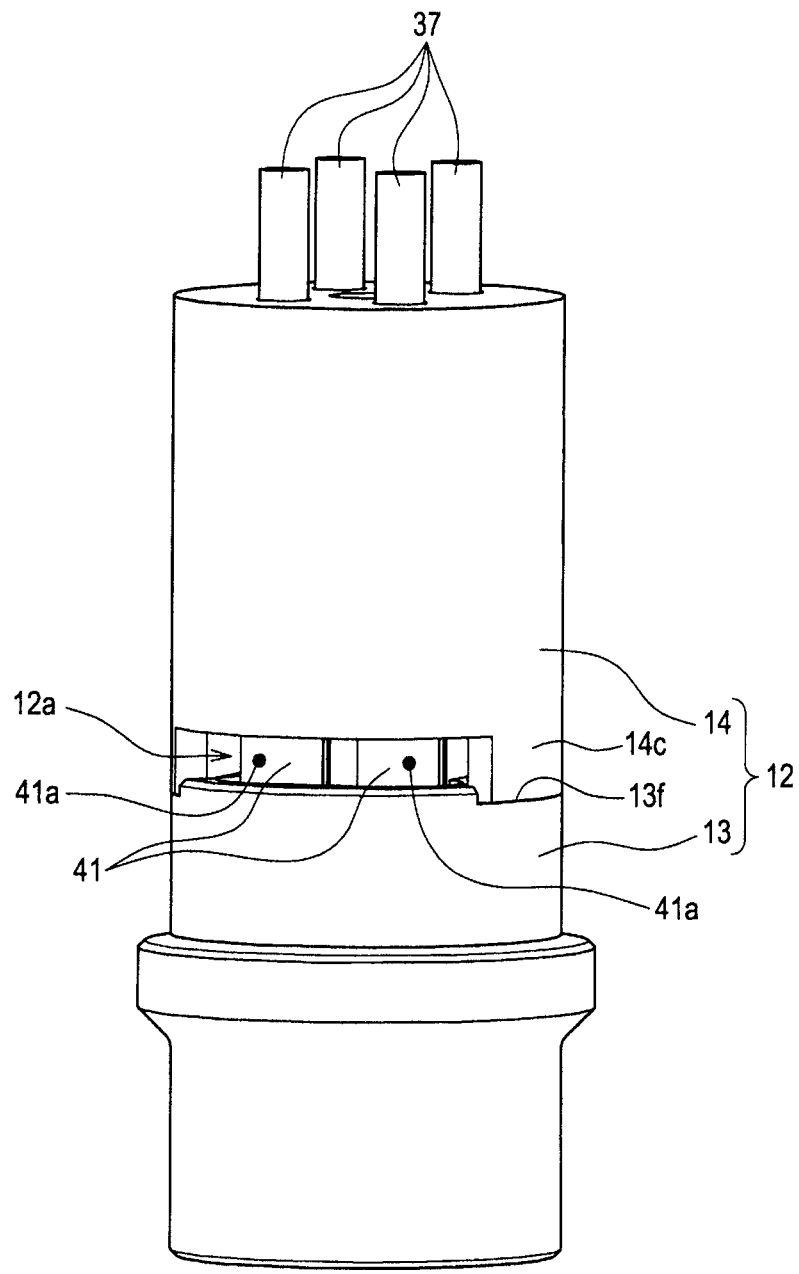
FIG. 8 is an explanatory exterior view showing an insulating separator with metal terminals disposed inside and the forward separator and the rear separator assembled together.

FIG. 8 is an explanatory exterior view showing an insulating separator 12 with the metal terminals 41 disposed inside and the forward separator 13 and the rear separator 14 assembled together.

The forward separator 13 and the rear separator 14 are assembled in such a manner that the two protrusions 14c of the rear separator 14 are engaged with the two recesses 13f, respectively, of the forward separator 13, thereby forming the insulating separator 12.

The insulating separator 12 is assembled, for example, as follows. First, a rear end portion of the detection element 5 and the four forward terminal members 43 are disposed in the terminal disposition hole 13b of the forward separator 13. Meanwhile, the lead wires 37 are inserted through the four terminal disposition holes 14b, respectively, of the rear separator 14; then, the cores 37a of the lead wires 37 are connected (fixed) to the signal-wire connection portions 45a of the rear terminal members 45, respectively, by crimping. Subsequently, the four rear terminal members 45 are connected to the four respective forward terminal members 43 disposed in the terminal disposition hole 13b of the forward separator 13; then, the rear separator 14 is moved toward the rear terminal members 45 along the lead wires 37, thereby accommodating (disposing) the four rear terminal members 45 in the terminal disposition holes 14b, respectively. At this time, the two protrusions 14c of the rear separator 14 are engaged with the two recesses 13f of the forward separator 13, respectively.

By this procedure, the forward separator 13 and the rear separator 14 are assembled together, thereby completing the insulating separator 12.

The insulating separator 12 has a ventilation path 12a in the form of a space defined by the protrusions 14c between the forward separator 13 and the rear separator 14.

Figure 9:
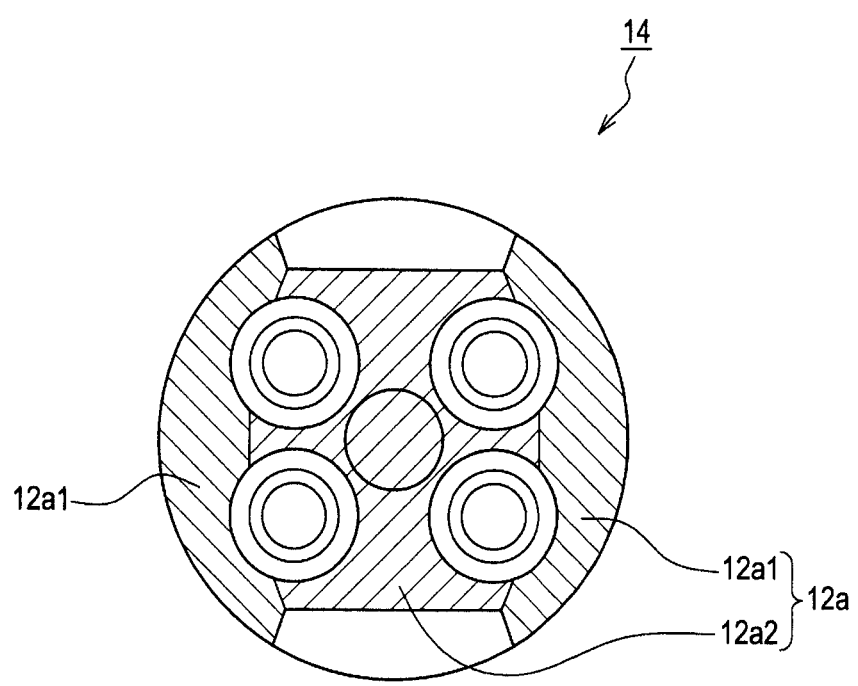
FIG. 9 is an explanatory view showing a side space and an inner space of a ventilation path of the insulating separator.

As shown in the explanatory view of FIG. 9, the ventilation path 12a includes a side space 12a1 extending from the side surface of the insulating separator 12 to the metal terminals 41, and an inner space 12a2 extending to all the metal terminals 41.

After completion of the insulating separator 12, welding is performed on those portions of the metal terminals 41 (the forward terminal members 43 and the rear terminal members 45) disposed within the insulating separator 12 which are exposed outward through the ventilation path 12a, thereby forming the weld zones 41a. Welding is performed on all of the four metal terminals 41 (the four forward terminal members 43 and the four rear terminal members 45).

[1-4. Effect]

As described above, in the gas sensor 1 of the present embodiment, the insulating separator 12 is formed to be dividable into the forward separator 13 having the terminal disposition hole 13b, and the rear separator 14 having the four terminal disposition holes 14b.

The forward separator 13 has the terminal disposition hole 13b for disposing therein a rear end portion of the detection element 5 and the four forward terminal members 43. One of the terminal disposition holes 14b of the rear separator 14 is adapted to dispose therein one of the rear terminal members 45. As a result of the rear separator 14 having the four terminal disposition holes 14b, the four rear terminal members 45 can be disposed in the rear separator 14.

In a state in which the forward terminal members 43 and the rear terminal members 45 are connected and in which the forward separator 13 and the rear separator 14 are assembled together, the insulating separator 12 has the ventilation path 12a formed between the forward separator 13 and the rear separator 14. The ventilation path 12a has side spaces 12a1 and the inner space 12a2. The side spaces 12a1 of the ventilation path 12a extend from the side surface of the forward separator 13 or from the side surface of the rear separator 14 to a plurality of the metal terminals 41.

As a result of the insulating separator 12 having the ventilation path 12a (more specifically, the side spaces 12a1) as mentioned above, moisture and the like which enter the insulating separator 12 from the forward side of the forward separator 13 through the terminal disposition hole 13b can be discharged outward of the insulating separator 12 through the ventilation path 12a (more specifically, the side spaces 12a1). As a result, corrosion of the metal terminals 41 caused by entry of moisture can be reduced, whereby transmission of a sensor signal and application of current or voltage through the metal terminals 41 can be appropriately implemented.

Thus, the gas sensor 1 can restrain corrosion of the metal terminals 41 caused by moisture through employment of the insulating separator 12 having the ventilation path 12a.

Next, in the gas sensor 1, the rear separator 14 has a plurality of the terminal disposition holes 14b. Each of the terminal disposition holes 14b is formed so as to dispose therein one of the rear terminal members 45 and has a sectional shape taken perpendicularly to the direction of insertion of the rear terminal member 45 identical to the sectional shape of the rear terminal member 45.

As a result of the terminal disposition holes 14b having such a shape, in inserting the rear terminal member 45 into the terminal disposition hole 14b, the relative position of the rear terminal member 45 in relation to the terminal disposition hole 14b (in other words, the relative position in the direction of rotation about the direction of insertion) can be determined on the basis of the sectional shape. Accordingly, the relative position of the rear terminal member 45 in relation to the terminal disposition hole 14b can be easily determined, thereby facilitating the work of inserting the rear terminal member 45 into the terminal disposition hole 14b.

Particularly, since the terminal disposition holes 14b and the rear terminal members 45 have circular sectional shapes, despite a change in the relative position of the rear terminal member 45 in the direction of rotation about the direction of insertion of the rear terminal member 45 in relation to the terminal disposition hole 14b, the relative position suited for the work of insertion can be maintained at all times. As a result, since the work of insertion can be easily performed without need to strictly adjust the relative position (the relative position in the direction of rotation) of the rear terminal member 45 in relation to the terminal disposition hole 14b, complication of the work of insertion can be mitigated.

Next, in the gas sensor 1, the insulating separator 12 has the ventilation path 12a formed therein and having the inner space 12a2 extending to at least two of the metal terminal members 41.

As a result of the insulating separator 12 having the ventilation path 12a formed therein and having the inner space 12a2 in addition to the side spaces 12a1 extending from the side surface to the metal terminals 41, ventilation within the insulating separator 12 is further improved, thereby facilitating discharge of moisture.

Therefore, the gas sensor 1 equipped with the insulating separator 12 having the side spaces 12a1 and the inner space 12a2 can further restrain corrosion of the metal terminals 41 caused by moisture.

Particularly, the inner space 12a2 is formed in such a manner as to extend to all the metal terminals 41. As a result of the inner space 12a2 having such a structure, ventilation within the insulating separator 12 is further improved, whereby stagnation of moisture around the metal terminals 41 can be restrained.

Next, in the gas sensor 1, the metal terminal 41 has the weld zone 41a for joining the forward terminal member 43 and the rear terminal member 45 together.

As a result of the metal terminal 41 having the weld zone 41a, a physical separation between the forward terminal member 43 and the rear terminal member 45 can be restrained, whereby an electrical connection between the forward terminal member 43 and the rear terminal member 45 can be maintained in a better condition.

Next, in the gas sensor 1, the rear separator 14 has the ventilation through hole 14d extending therethrough between the forward side and the rear side.

As a result of the rear separator 14 having the ventilation through hole 14d as mentioned above, since moisture existing within the insulating separator 12 can be discharged outward through the ventilation through hole 14d, ventilation is further improved.

Next, the metal terminal 41 is composed of the forward terminal member 43 having the element contact portion 43e, and the rear terminal member 45 having the signal-wire connection portion 45a. The forward terminal member 43 has the female connection portion 43b. The rear terminal member 45 has the male connection portion 45b to be connected to the female connection portion 43b. The forward terminal member 43 and the rear terminal member 45 electrically connect the electrode terminal portion 31, 32, 34, or 35 of the detection element 5 and the lead wire 37 as a result of the male connection portion 45b and the female connection portion 43b being connected together.

Since, at a stage prior to connecting the forward terminal member 43 and the rear terminal member 45 together, the metal terminal 41 having such a structure allows the work of bringing the element contact portion 43e (the forward terminal member 43) into contact with the electrode terminal portion 31, 32, 34, or 35 and the work of connecting the signal-wire connection portion 45a (the rear terminal member 45) to the lead wire 37 to be performed separately, working is possible even in a state in which the detection element 5 and the lead wire 37 are separated from each other. By connecting together the forward terminal member 43 in contact with the electrode terminal portion 31, 32, 34, or 35 and the rear terminal member 45 connected to the lead wire 37, the electrode terminal portion 31, 32, 34, or 35 and the lead wire 37 can be electrically connected.

Use of the metal terminals 41 each having the forward terminal member 43 and the rear terminal member 45 as mentioned above can mitigate complication of the work of electrically connecting the electrode terminal portions 31, 32, 34, and 35 and the respective lead wires 37.

[1-5. Terminological Correspondence]

The terminological correspondence between the present embodiment and claims will be described.

The gas sensor 1 corresponds to an example of the gas sensor; the detection element 5 corresponds to an example of the sensor element; the metal terminal 41 corresponds to an example of the metal terminal; the lead wire 37 corresponds to an example of the signal wire; and the insulating separator 12 corresponds to an example of the terminal insulation member.

The forward terminal member 43 corresponds to an example of the forward terminal member; the rear terminal member 45 corresponds to an example of the rear terminal member; the female connection portion 43b corresponds to an example of the female connection portion; the male connection portion 45b corresponds to an example of the male connection portion; the element contact portion 43e corresponds to an example of the element contact portion; the signal-wire connection portion 45a corresponds to an example of the signal-wire connection portion; and the weld zone 41a corresponds to an example of the weld zone.

The forward separator 13 corresponds to an example of the forward insulation member, and the terminal disposition hole 13b corresponds to an example of the terminal disposition hole. The rear separator 14 corresponds to an example of the rear insulation member, and the terminal disposition hole 14b corresponds to an example of the terminal disposition hole. The side space 12a1 of the ventilation path 12a corresponds to an example of the side ventilation path; the inner space 12a2 of the ventilation path 12a corresponds to an example of the inter-terminal ventilation path; and the ventilation through hole 14d corresponds to an example of the ventilation through hole.

[2. Second Embodiment]

[2-1. Overall Configuration]

A second embodiment will be described while referring to a gas sensor having second metal terminals 141 and a second insulating separator 112.

The second metal terminal 141 differs from the metal terminal 41 of the first embodiment in the sectional shapes of a female connection portion and a male connection portion. The second insulating separator 112 differs from the insulating separator 12 (more specifically, the ventilation through hole 14d of the rear separator 14) of the first embodiment in the sectional shape of the terminal disposition hole of the rear insulation member.

Since the second embodiment differs from the first embodiment in the structures of the metal terminal and the insulating separator, the second embodiment will be described, centering on the metal terminal and the insulating separator. In the following description of the second embodiment, structural features similar to those of the first embodiment will be described by use of reference numerals similar to those of the first embodiment, or description thereof will be omitted.

[2-2. Second Metal Terminal]

First, the second metal terminal 141 will be described.

Figure 10:
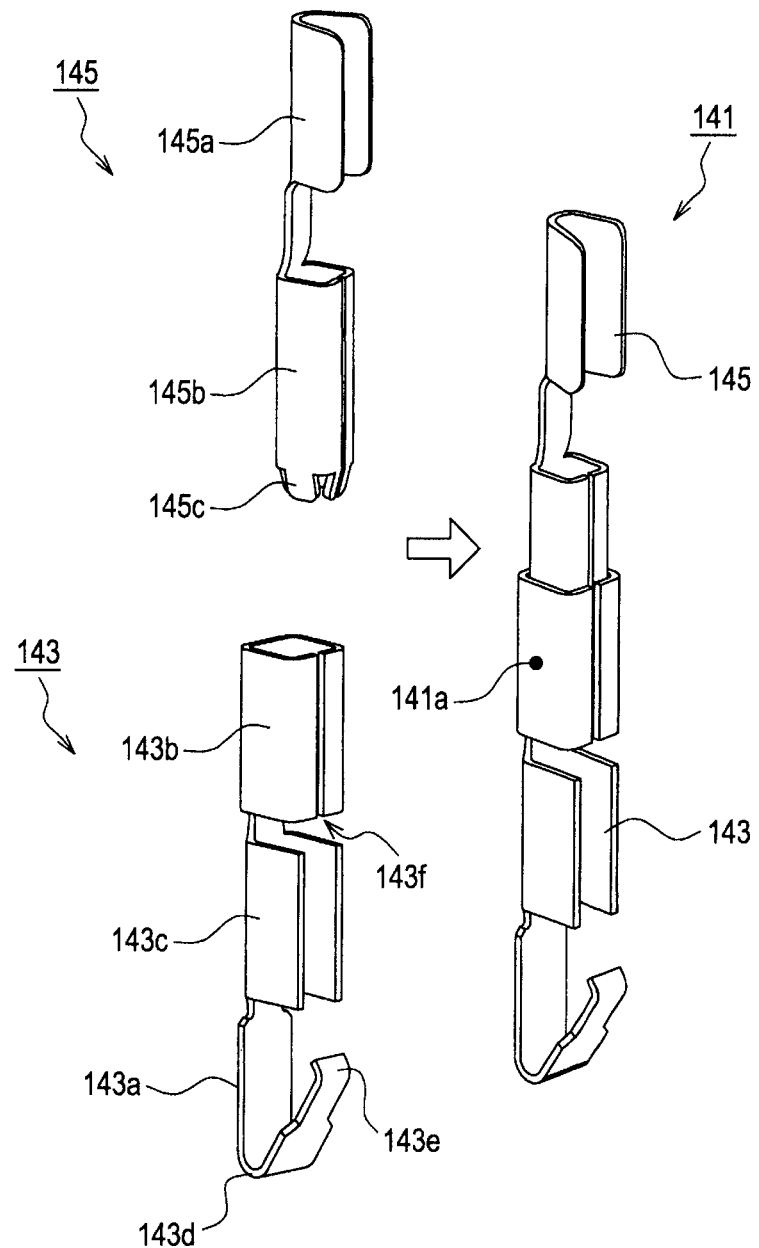
FIG. 10 is an explanatory view showing the structure of a second metal terminal composed of a second forward terminal member and a second rear terminal member.

FIG. 10 is an explanatory view showing the structure of the second metal terminal 141.

The second metal terminal 141 is composed of a second forward terminal member 143 and a second rear terminal member 145. That is, the second metal terminal 141 is not a single member, but can be divided into the second forward terminal member 143 and the second rear terminal member 145.

The second forward terminal member 143 is formed of a metal material which can maintain elasticity (spring elasticity) even in repeated exposure to high temperature; for example, an alloy material which predominantly contains Ni (NCF718 or the like). The second forward terminal member 143 is formed by bending an elongated sheet-like metal material and includes a body portion 143a, a female connection portion 143b, extension portions 143c, a bend portion 143d, and an element contact portion 143e.

Since the body portion 143a, the extension portions 143c, the bend portion 143d, and the element contact portion 143e of the second forward terminal member 143 are similar in structure to the body portion 43a, the extension portions 43c, the bend portion 43d, and the element contact portion 43e, respectively, of the forward terminal member 43 of the first embodiment, description thereof is omitted.

The female connection portion 143b is located rearward of the body portion 143a, has a tubular shape, and has a regular polygonal section (specifically, a square section) taken perpendicularly to the axial direction. The female connection portion 143b has a slit 143f for allowing a change of the inside diameter of the tubular shape in response to elastic deformation. Thus, the sectional shape of the female connection portion 143b is strictly a regular polygon with a break.

The second forward terminal member 143 having such a structure can maintain contact between the element contact portion 143e and the detection element 5 through elastic deformation of the bend portion 143d resulting from contact of the element contact portion 143e with the detection element 5 (specifically, the electrode terminal portion 31, 32, 34, or 35).

Next, the second rear terminal member 145 is formed of a metal material, such as a stainless steel alloy (SUS304), smaller in "0.2% yield strength" than a metal material used to form the second forward terminal member 143. The second rear terminal member 145 is formed by bending an elongated sheet-like metal material and includes a signal-wire connection portion 145a and a male connection portion 145b.

Since the signal-wire connection portion 145a of the second rear terminal member 145 is similar in structure to the signal-wire connection portion 45a of the rear terminal member 45 of the first embodiment, description thereof is omitted.

The male connection portion 145b is located forward of the signal-wire connection portion 145a, has a tubular shape, and has a regular polygonal section (specifically, a square section) taken perpendicularly to the axial direction. The male connection portion 145b has such an outside diameter as to allow insertion thereof into the female connection portion 143b. The male connection portion 145b has a forward-end diameter-reducing portion 145c. The diameter-reducing portion 145c is shaped such that the diameter reduces forward.

The second rear terminal member 145 having such a structure is electrically connected to external equipment through the lead wire 37 as a result of the signal-wire connection portion 145a being electrically connected to the core 37a of the lead wire 37.

As shown at the right of FIG. 10, the second metal terminal 141 is configured such that the second forward terminal member 143 and the second rear terminal member 145 are connected together. More specifically, the second metal terminal 141 composed of the second forward terminal member 143 and the second rear terminal member 145 is formed through connection of the male connection portion 145b and the female connection portion 143b.

The second metal terminal 141 having such a structure is configured such that the element contact portion 143e of the second forward terminal member 143 is electrically connected to the detection element 5 (specifically, the electrode terminal portion 31, 32, 34, or 35) while the signal-wire connection portion 145a of the second rear terminal member 145 is electrically connected to external equipment through the lead wire 37.

The second forward terminal member 143 is formed of an alloy material which predominantly contains Ni, and the second rear terminal member 145 is formed of a stainless steel alloy. An alloy material which predominantly contains Ni is superior in heat resistance to and greater in "0.2% yield strength" than a stainless steel alloy. That is, the second forward terminal member 143 is formed of a material superior in heat resistance to and larger in elastic deformation region than a material used to form the second rear terminal member 145.

The second metal terminal 141 has a weld zone 141a for joining the male connection portion 145b and the female connection portion 143b together. As a result of the second metal terminal 141 having the weld zone 141a, a physical separation between the second forward terminal member 143 and the second rear terminal member 145 can be restrained, whereby an electrical connection between the second forward terminal member 143 and the second rear terminal member 145 can be maintained in a better condition.

[2-3. Second Insulating Separator]

Next, a second insulating separator 112 provided in a gas sensor of the second embodiment will be described.

The second insulating separator 112 is formed to be dividable into the forward separator 13 and a second rear separator 114.

That is, as compared with the insulating separator 12 of the first embodiment, the second insulating separator 112 is composed of the same forward separator 13 and the second rear separator 114 in place of the rear separator 14.

Since the second rear separator 114 is similar in exterior appearance to the rear separator 14, the exterior appearance of the second insulating separator 112 is similar to that of the insulating separator 12 of the first embodiment (see FIG. 8).

The second rear separator 114 is a tubular member formed of an insulating material (e.g., alumina).

Figure 11:
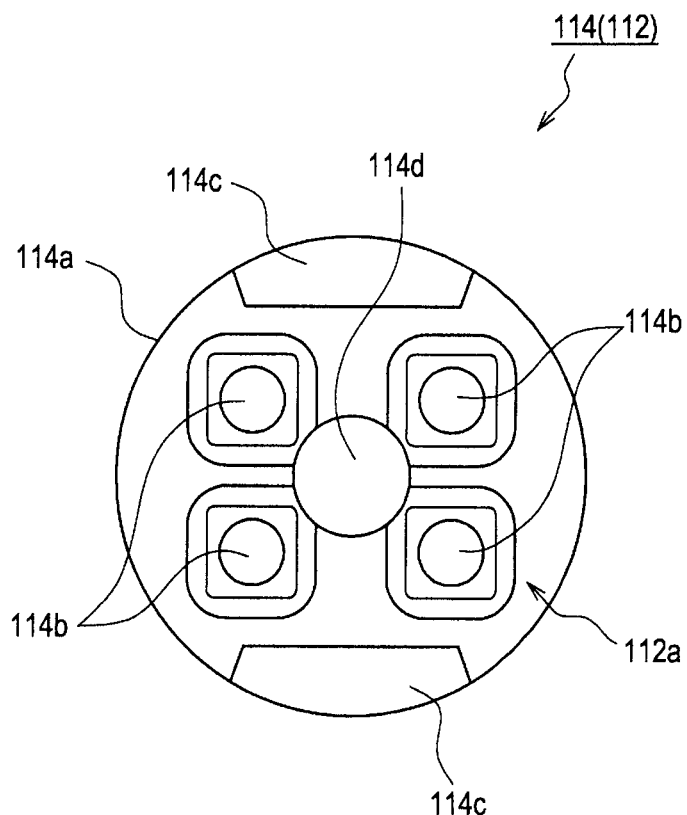
FIG. 11 is an exterior view of a second rear separator as viewed from the forward side.

FIG. 11 is an exterior view of the second rear separator 114 as viewed from the forward side.

As shown in FIG. 11, the second rear separator 114 includes a tubular separator body portion 114a and protrusions 114c.

The separator body portion 114a has a plurality of (four in the present embodiment) terminal disposition holes 114b extending therethrough in the axial direction. Each of the terminal disposition holes 114b has a regular polygonal section (specifically, a square section) taken perpendicularly to the axial direction and has such a size as to accommodate a rear end portion (the second rear terminal member 145) of the second metal terminal 141. In the second rear separator 114, a single second metal terminal 141 is disposed in a single terminal disposition hole 114b, thereby preventing contact (electrical short circuit) between the second metal terminals 141 (more specifically, the second rear terminal members 145).

The separator body portion 114a also has a ventilation through hole 114d extending therethrough in the axial direction. By virtue of the second rear separator 114 having the ventilation through hole 114d, moisture or the like existing between the forward separator 13 and the second rear separator 114 can be discharged outward through the ventilation through hole 114d. The plug member 15 has a ventilation hole (not shown in FIG. 1) communicating with the ventilation through hole 114d and with the outside.

The protrusions 114c protrude forward from the forward end of the separator body portion 114a. The two protrusions 114c are formed at the forward end of the separator body portion 114a.

That is, the second rear separator 114 is similar in exterior appearance to the rear separator 14, but the sectional shape of the terminal disposition holes 114b differs from that of the terminal disposition holes 14b. The second insulating separator 112 has a ventilation path 112a in the form of a space defined by the protrusions 114c between the forward separator 13 and the second rear separator 114.

Figure 12:
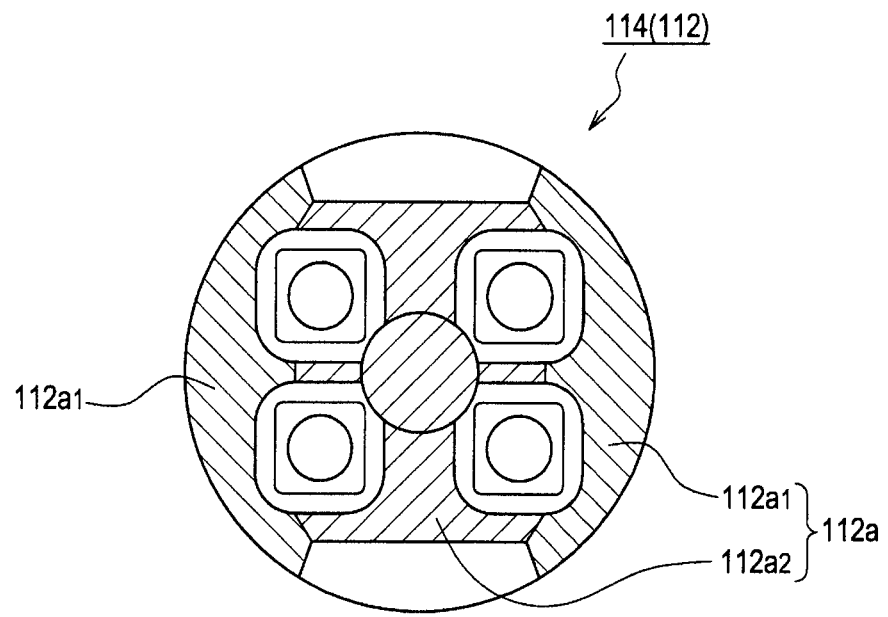
FIG. 12 is an explanatory view showing a side space and an inner space of a ventilation path of a second insulating separator.

As shown in the explanatory view of FIG. 12, the ventilation path 112a has side spaces 112a1 extending from the side surface of the second insulating separator 112 to the internal second metal terminals 141 (the terminal disposition holes 114b), and an inner space 112a2 extending to all the second metal terminals 141 (the terminal disposition holes 114b).

After completion of the second insulating separator 112, welding is performed on those portions of the second metal terminals 141 (the second forward terminal members 143 and the second rear terminal members 145) disposed within the second insulating separator 112 which are exposed outward through the ventilation path 112a, thereby forming the weld zones 141a. Welding is performed on all of the four second metal terminals 141 (the four second forward terminal members 143 and the four second rear terminal members 145).

[2-4. Effect]

As described above, in the gas sensor of the second embodiment, the second insulating separator 112 is formed to be dividable into the forward separator 13 having the terminal disposition hole 13b, and the second rear separator 114 having the four terminal disposition holes 114b.

The second insulating separator 112 has the ventilation path 112a formed between the forward separator 13 and the second rear separator 114. The ventilation path 112a has the side spaces 112a1 and the inner space 112a2. The side spaces 112a1 of the ventilation path 112a extend from the side surface of the forward separator 13 or from the side surface of the second rear separator 114 to a plurality of the metal terminals 41.

As a result of the second insulating separator 112 having the ventilation path 112a (more specifically, the side spaces 112a1) as mentioned above, moisture and the like which enter the second insulating separator 112 from the forward side of the forward separator 13 through the terminal disposition hole 13b can be discharged outward of the second insulating separator 112 through the ventilation path 112a (more specifically, the side spaces 112a1). As a result, corrosion of the second metal terminals 141 caused by entry of moisture can be reduced, whereby transmission of a sensor signal and application of current or voltage through the second metal terminals 141 can be appropriately implemented.

Thus, the gas sensor can restrain corrosion of the second metal terminals 141 caused by moisture through employment of the second insulating separator 112 having the ventilation path 112a.

Next, the second rear separator 114 has a plurality of the terminal disposition holes 114b. Each of the terminal disposition holes 114b is formed so as to dispose therein one of the second rear terminal members 145 and has a sectional shape taken perpendicularly to the direction of insertion of the second rear terminal member 145 identical to the sectional shape of the second rear terminal member 145.

As a result of the terminal disposition holes 114b having such a shape, in inserting the second rear terminal member 145 into the terminal disposition hole 114b, the relative position of the second rear terminal member 145 in relation to the terminal disposition hole 114b (in other words, the relative position in the direction of rotation about the direction of insertion) can be determined on the basis of the sectional shape. Accordingly, the relative position of the second rear terminal member 145 in relation to the terminal disposition hole 114b can be easily determined, thereby facilitating the work of inserting the second rear terminal member 145 into the terminal disposition hole 114b.

[2-5. Terminological Correspondence]

The terminological correspondence between the present embodiment and claims will be described.

The second insulating separator 112 corresponds to an example of the terminal insulation member. The forward separator 13 corresponds to an example of the forward insulation member, and the terminal disposition hole 13b corresponds to an example of the terminal disposition hole. The second rear separator 114 corresponds to an example of the rear insulation member, and the terminal disposition hole 114b corresponds to an example of the terminal disposition hole. The side space 112a1 of the ventilation path 112a corresponds to an example of the side ventilation path; the inner space 112a2 of the ventilation path 112a corresponds to an example of the inter-terminal ventilation path; and the ventilation through hole 114d corresponds to an example of the ventilation through hole.

The second metal terminal 141 corresponds to an example of the metal terminal; the second forward terminal member 143 corresponds to an example of the forward terminal member; the second rear terminal member 145 corresponds to an example of the rear terminal member; the female connection portion 143b corresponds to an example of the female connection portion; the male connection portion 145b corresponds to an example of the male connection portion; the element contact portion 143e corresponds to an example of the element contact portion; and the signal-wire connection portion 145a corresponds to an example of the signal-wire connection portion.

[3. Other Embodiments]

While the present invention has been described with reference to the above embodiments, the present invention is not limited thereto, but may be embodied in various other forms without departing from the gist of the invention.

Figure 13:
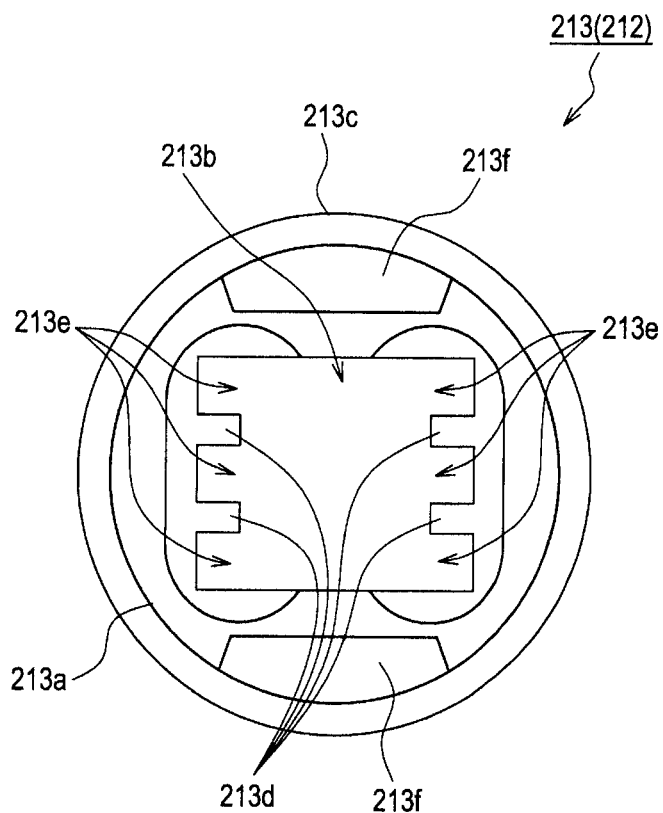
FIG. 13 is an exterior view of a third forward separator as viewed from the rear side.
Figure 14:
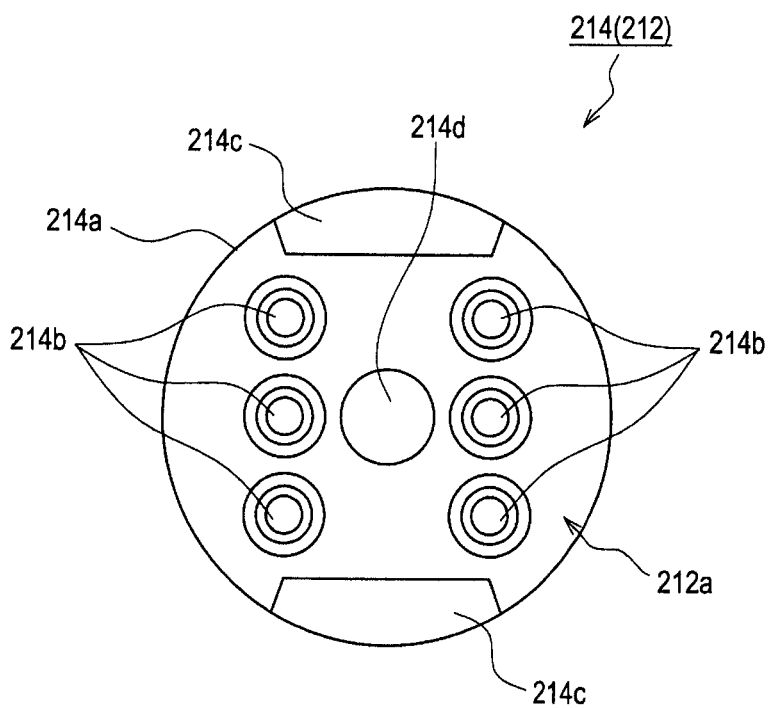
FIG. 14 is an exterior view of a third rear separator as viewed from the forward side.

For example, the above embodiments are described while referring to the terminal insulation member (the insulating separator) within which four metal terminals are disposed. However, the number of the metal terminals disposed within the terminal insulation member is not limited to four, but can be selected according to the number of the electrode terminal portions of the sensor element (two, three, five, six, etc.). For example, a third insulating separator 212 has a structure in which six metal terminals 41 are disposed therein. The third insulating separator 212 is formed to be dividable into a third forward separator 213 having six terminal disposition regions 213e as shown in FIG. 13, and a third rear separator 214 having six terminal disposition holes 214b as shown in FIG. 14.

The third forward separator 213 differs from the above-mentioned forward separator 13 in the number of partitions 213d; specifically, a terminal disposition hole 213b has the six terminal disposition regions 213e formed therein. The third forward separator 213 includes a tubular separator body portion 213a and a collar portion 213c. The third forward separator 213 also includes two recesses 213f formed at the rear end of the separator body portion 213a.

The third rear separator 214 includes a tubular separator body portion 214a and protrusions 214c. The separator body portion 214a has a ventilation through hole 214d extending therethrough in the axial direction. The two protrusions 214c are formed at the forward end of the separator body portion 214a in such a manner as to protrude forward.

The third insulating separator 212 has a ventilation path 212a in the form of a space defined by the protrusions 214c between the third forward separator 213 and the third rear separator 214.

Similar to the above-mentioned insulating separator 12, as a result of the thus-configured third insulating separator 212 having the ventilation path 212a, moisture and the like which enter the third insulating separator 212 from the forward side of the third forward separator 213 through the terminal disposition hole 213b can be discharged outward of the third insulating separator 212 through the ventilation path 212a. As a result, corrosion of the metal terminals 41 caused by entry of moisture can be reduced, whereby transmission of a sensor signal and application of current or voltage through the metal terminals 41 can be appropriately implemented.

Figure 15:
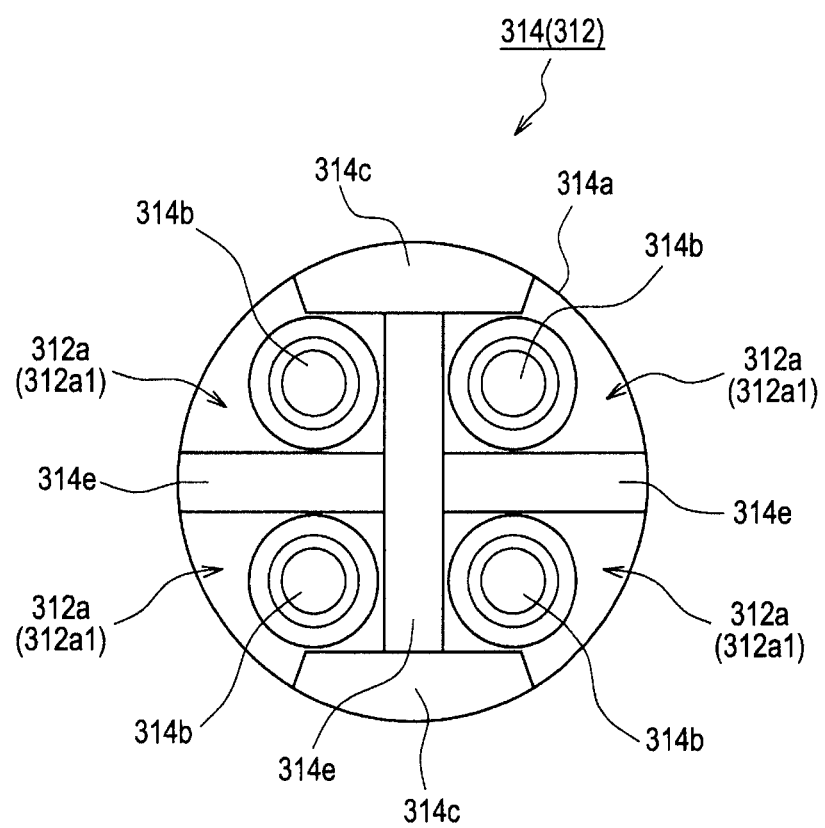
FIG. 15 is an exterior view of a fourth rear separator as viewed from the forward side.

Next, the above embodiments are described while referring to the terminal insulation member (the insulating separator) having the ventilation path 12a composed of the side spaces 12a1 and the inner space 12a2. However, the structure of the terminal insulation member is not limited thereto. For example, as shown in FIG. 15, the insulating separator may assume the form of a fourth insulating separator 312 having ventilation paths 312a having side spaces 312a1 only. The fourth insulating separator 312 is formed to be dividable into the forward separator 13 and a fourth rear separator 314.

Since the forward separator 13 is similar in structure to that of the first embodiment, description thereof is omitted.

The fourth rear separator 314 includes a tubular separator body portion 314a, protrusions 314c, and a center partition 314e. The separator body portion 314a has four terminal disposition holes 314b. The two protrusions 314c are formed at the forward end of the separator body portion 314a in such a manner as to protrude forward. The center partition 314e protrudes forward from the forward end of the separator body portion 314a and divides the forward end region of the separator body portion 314a into four ventilation paths 312a. The shape of the center partition 314e is determined so as to dispose one terminal disposition hole 314b in relation to one ventilation path 312a. The center partition 314e of the fourth rear separator 314 assumes a + shape (a plus shape). The four ventilation paths 312a have the respective side spaces 312a1 extending from the side surface of the fourth insulating separator 312 to the internal metal terminals 41 (the terminal disposition holes 314b).

Similar to the above-mentioned insulating separator 12, as a result of the thus-configured fourth insulating separator 312 having the ventilation paths 312a, moisture and the like which enter the fourth insulating separator 312 from the forward side of the forward separator 13 through the terminal disposition hole 13b can be discharged outward of the fourth insulating separator 312 through the ventilation paths 312a. As a result, corrosion of the metal terminals 41 caused by entry of moisture can be reduced, whereby transmission of a sensor signal and application of current or voltage through the metal terminals 41 can be appropriately implemented.

Figure 16:
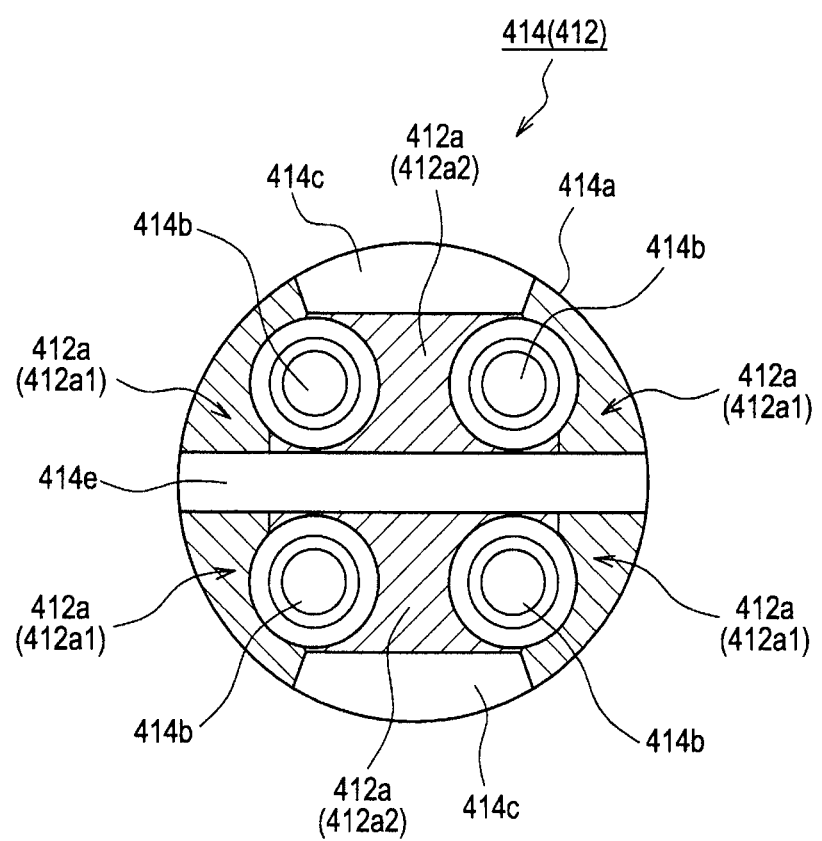
FIG. 16 is an exterior view of a fifth rear separator as viewed from the forward side.

Next, another embodiment of the terminal insulation member (the insulating separator) may assume, for example, as shown in FIG. 16, the form of a fifth insulating separator 412 having ventilation paths 412a in the form of spaces each communicating with two terminal disposition holes 414b. The fifth insulating separator 412 is formed to be dividable into the forward separator 13 and a fifth rear separator 414.

Since the forward separator 13 is similar in structure to that of the first embodiment, description thereof is omitted.

The fifth rear separator 414 includes a tubular separator body portion 414a, protrusions 414c, and a center partition 414e. The separator body portion 414a has four terminal disposition holes 414b. The two protrusions 414c are formed at the forward end of the separator body portion 414a in such a manner as to protrude forward. The center partition 414e protrudes forward from the forward end of the separator body portion 414a and divides the forward end region of the separator body portion 414a into two ventilation paths 412a. The shape of the center partition 414e is determined so as to dispose two terminal disposition holes 414b in relation to one ventilation path 412a. The center partition 414e of the fifth rear separator 414 is formed to extend straight, perpendicular to an imaginary line which connects the two protrusions 414c, at an intermediate position between the two protrusions 414c.

Each of the two ventilation paths 412a has side spaces 412a1 and an inner space 412a2. The side spaces 412a1 extend from the side surface of the fifth insulating separator 412 to the respective internal metal terminals 41 (the terminal disposition holes 414b). The inner space 412a2 extends to the two metal terminals 41 (the two terminal disposition holes 414b).

Similar to the above-mentioned insulating separator 12, as a result of the thus-configured fifth insulating separator 412 having the two ventilation paths 412a, moisture and the like which enter the fifth insulating separator 412 from the forward side of the forward separator 13 through the terminal disposition hole 13b can be discharged outward of the fifth insulating separator 412 through the two ventilation paths 412a. As a result, corrosion of the metal terminals 41 caused by entry of moisture can be reduced, whereby transmission of a sensor signal and application of current or voltage through the metal terminals 41 can be appropriately implemented.

Figure 17:
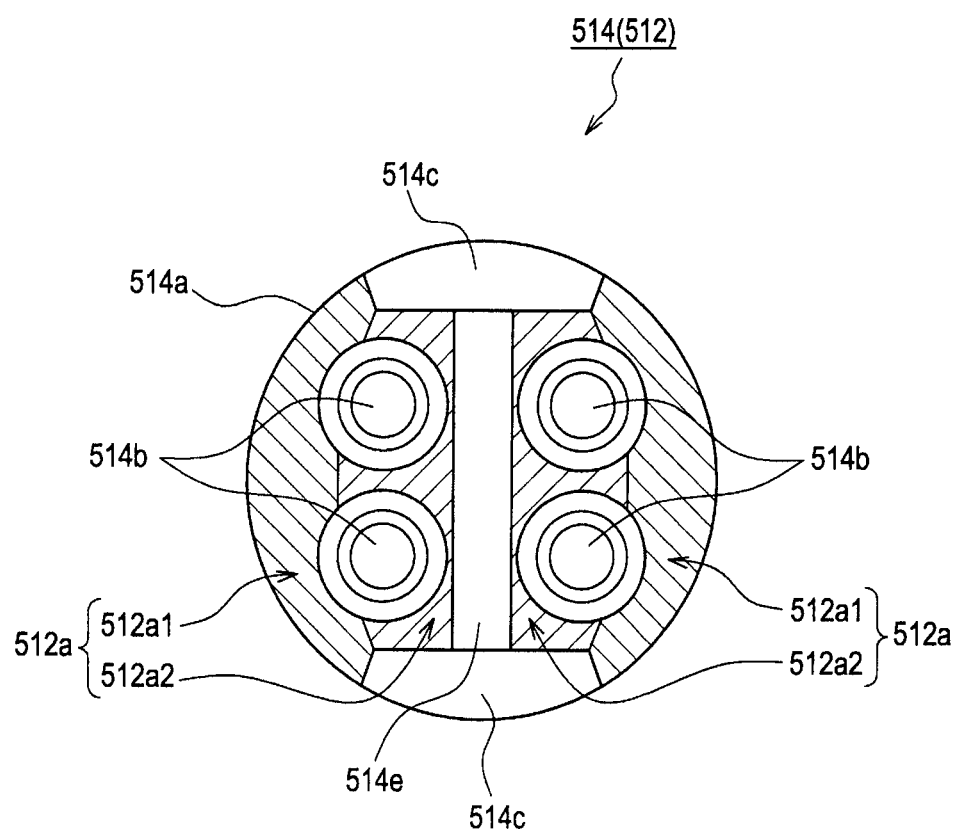
FIG. 17 is an exterior view of a sixth rear separator as viewed from the forward side.

Next, still another embodiment of the terminal insulation member (the insulating separator) may assume, for example, as shown in FIG. 17, the form of a sixth insulating separator 512 having ventilation paths 512a in the form of spaces each communicating with two terminal disposition holes 514b. The sixth insulating separator 512 is formed to be dividable into the forward separator 13 and a sixth rear separator 514.

Since the forward separator 13 is similar in structure to that of the first embodiment, description thereof is omitted.

The sixth rear separator 514 includes a tubular separator body portion 514a, protrusions 514c, and a center partition 514e. The separator body portion 514a has four terminal disposition holes 514b. The two protrusions 514c are formed at the forward end of the separator body portion 514a in such a manner as to protrude forward. The center partition 514e protrudes forward from the forward end of the separator body portion 514a and divides the forward end region of the separator body portion 514a into two ventilation paths 512a. The shape of the center partition 514e is determined so as to dispose two terminal disposition holes 514b in relation to one ventilation path 512a. The center partition 514e of the sixth rear separator 514 is formed rectilinearly such that its ends are connected to the two protrusions 514c, respectively.

Each of the two ventilation paths 512a has a side space 512a1 and an inner space 512a2. The side space 512a1 extends from the side surface of the sixth insulating separator 512 to the internal metal terminals 41 (the terminal disposition holes 514b). The inner space 512a2 extends to the two metal terminals 41 (the two terminal disposition holes 514b).

Similar to the above-mentioned insulating separator 12, as a result of the thus-configured sixth insulating separator 512 having the two ventilation paths 512a, moisture and the like which enter the sixth insulating separator 512 from the forward side of the forward separator 13 through the terminal disposition hole 13b can be discharged outward of the sixth insulating separator 512 through the two ventilation paths 512a. As a result, corrosion of the metal terminals 41 caused by entry of moisture can be reduced, whereby transmission of a sensor signal and application of current or voltage through the metal terminals 41 can be appropriately implemented.

Figure 18:
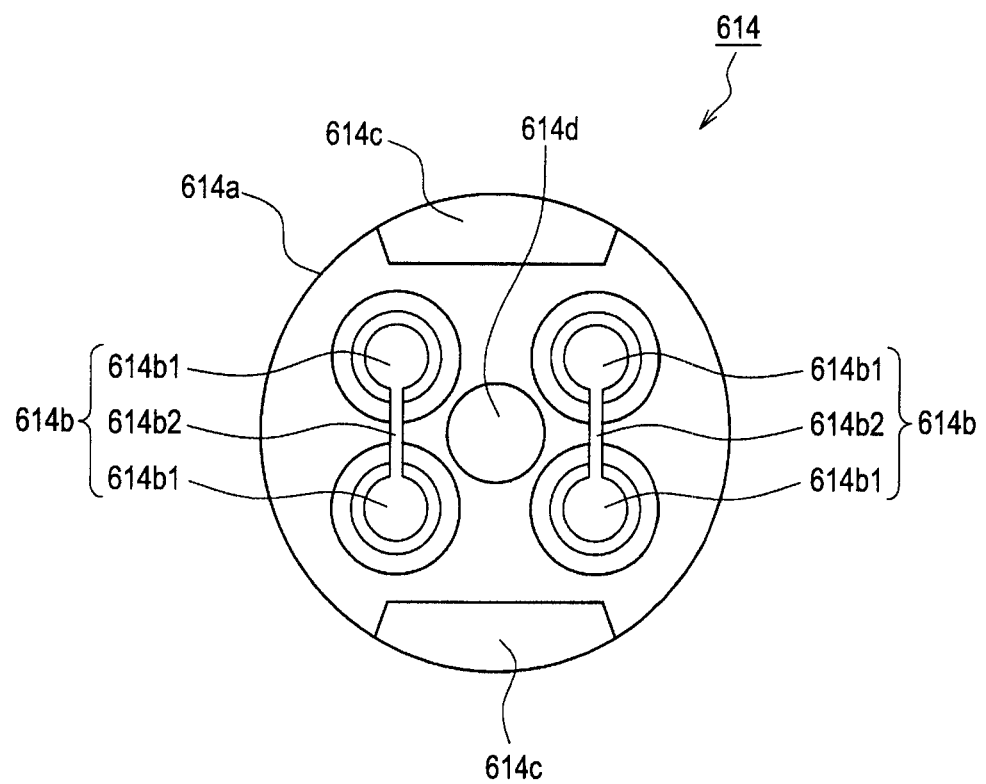
FIG. 18 is an exterior view of a seventh rear separator as viewed from the forward side.

Next, the above embodiments are described while referring to the rear insulation member (the rear separator) in which a single rear terminal member is disposed in a single terminal disposition hole. However, the structure of the rear insulation member (the rear separator) is not limited thereto. For example, as shown in FIG. 18, the rear insulation member may assume the form of a seventh rear separator 614 in which a plurality of (two) metal terminals 41 (more specifically, the rear terminal members 45) are disposed in a single terminal disposition hole 614b.

The seventh rear separator 614 includes a tubular separator body portion 614a and protrusions 614c.

The separator body portion 614a has two terminal disposition holes 614b. A single terminal disposition hole 614b has two terminal disposition regions 614b1 and a single gap region 614b2. Each of the two terminal disposition regions 614b1 has a circular section taken perpendicularly to the axial direction and has such a size as to accommodate a rear portion (the rear terminal member 45) of the metal terminal 41. The gap region 614b2 connects the two terminal disposition regions 614b1.

The protrusions 614c protrude forward from the forward end of the separator body portion 614a. The two protrusions 614c are formed at the forward end of the separator body portion 614a. The separator body portion 614a has a ventilation through hole 614d extending therethrough in the axial direction.

The seventh rear separator 614 having such a structure can have, in each of the terminal disposition holes 614b, not only the terminal disposition regions 614b1 for disposing therein rear portions (the rear terminal members 45) of the metal terminals 41, respectively, but also the gap region 614b2 not occupied by the rear portions (the rear terminal members 45) of the metal terminals 41. As a result, the seventh rear separator 614 easily discharge outward moisture generated therein through the gap regions 614b2 of the terminal disposition holes.

Therefore, the gas sensor equipped with the terminal insulation member having the seventh rear separator 614 can further restrain corrosion of the metal terminals 41 caused by moisture.

Figure 19:
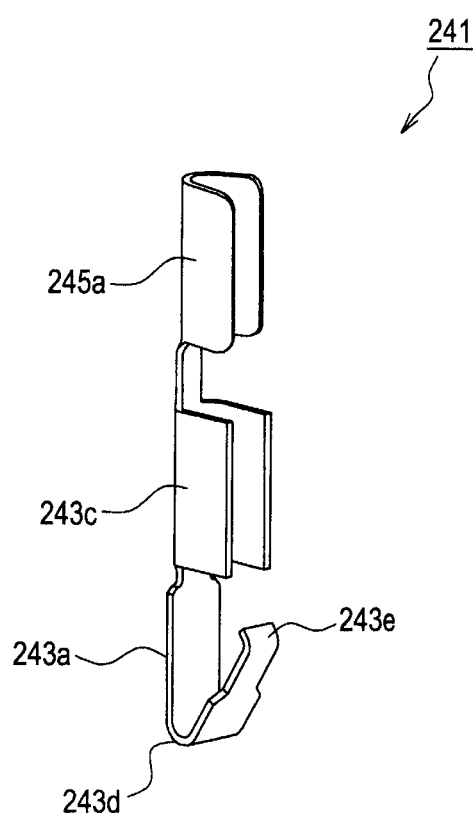
FIG. 19 is an explanatory exterior view of a third metal terminal.

Next, the above embodiments are described while referring to the metal terminal which is formed to be dividable into the forward terminal member and the rear terminal member. However, the structure of the metal terminal is not limited thereto. For example, the metal terminal may assume the form of a single member such as a third metal terminal 241 shown in FIG. 19. The third metal terminal 241 is formed of a metal material which can maintain elasticity (spring elasticity) even in repeated exposure to high temperature; for example, an alloy material which predominantly contains Ni (NCF718 or the like). The third metal terminal 241 is formed by bending an elongated sheet-like metal material and includes a body portion 243a, extension portions 243c, a bend portion 243d, an element contact portion 243e, and a signal-wire connection portion 245a. The body portion 243a, the extension portions 243c, the bend portion 243d, the element contact portion 243e, and the signal-wire connection portion 245a are similar in structure to the body portion 43a, the extension portions 43c, the bend portion 43d, the element contact portion 43e, and the signal-wire connection portion 45a, respectively, in the first embodiment.

DESCRIPTION OF REFERENCE NUMERALS

1: gas sensor; 3: metallic shell; 5: detection element; 9: element protector; 11: sleeve; 12: insulating separator; 12a: ventilation path; 12a1: side space; 12a2: inner space; 13: forward separator; 13b: terminal disposition hole; 13e: terminal disposition region; 14: rear separator; 14b: terminal disposition hole; 14c: protrusion; 14d: ventilation through hole; 31, 32, 34, 35: electrode terminal portion; 37: lead wire; 37a: core; 41: metal terminal; 41a: weld zone; 43: forward terminal member; 43b: female connection portion; 45: rear terminal member; 45b: male connection portion; 112: second insulating separator; 112a: ventilation path; 112a1: side space; 112a2: inner space; 114: second rear separator; 114b: terminal disposition hole; 114d: ventilation through hole; 141: second metal terminal; 141a: weld zone; 143: second forward terminal member; 143b: female connection portion; 145: second rear terminal member; 145b: male connection portion; 212: third insulating separator; 212a: ventilation path; 213: third forward separator; 213b: terminal disposition hole; 214: third rear separator; 214b: terminal disposition hole; 214d: ventilation through hole; 241: third metal terminal; 312: fourth insulating separator; 312a: ventilation path; 312a1: side space; 314: fourth rear separator; 314b: terminal disposition hole; 412: fifth insulating separator; 412a: ventilation path; 412a1: side space; 412a2: inner space; 414: fifth rear separator; 414b: terminal disposition hole; 512: sixth insulating separator; 512a: ventilation path; 512a1: side space; 512a2: inner space; 514: sixth rear separator; 514b: terminal disposition hole; 614: seventh rear separator; 614b: terminal disposition hole; 614b1: terminal disposition region; and 614b2; gap region.

The invention claimed is:

1. A gas sensor comprising:
a sensor element having a plurality of electrode terminal portions through which a detection signal indicative of a result of detection of a target gas is output from the sensor element to external equipment or through which current or voltage is input from the external equipment to the sensor element;
a plurality of metal terminals electrically connected to the respective electrode terminal portions of the sensor element;
a plurality of signal wires electrically connected to the respective metal terminals and forming signal paths for connecting the electrode terminal portions and the external equipment, and
a terminal insulation member that electrically insulates the metal terminals in contact with the respective electrode terminal portions from one another,
wherein each of the metal terminals includes an element contact portion in contact with the corresponding electrode terminal portion and a signal-wire connection portion connected to the corresponding signal wire;
the terminal insulation member is formed to be dividable into a forward insulation member having a terminal disposition hole for disposing therein at least a portion of the sensor element and at least the element contact portions of the metal terminals, and a rear insulation member having a terminal disposition hole for disposing therein at least the signal-wire connection portions of the metal terminals;
in a state in which the forward insulation member and the rear insulation member are assembled together and in which the metal terminals are disposed in the terminal disposition holes, the terminal insulation member has a side ventilation path formed between the forward insulation member and the rear insulation member and extending from a side surface of the forward insulation member or from a side surface of the rear insulation member to the metal terminals; and
the terminal insulation member has an inter-terminal ventilation path in the form of a space extending to at least two of the metal terminals.

2. The gas sensor according to claim 1, wherein
the rear insulation member has a plurality of the terminal disposition holes, and
at least one of the terminal disposition holes is formed so as to dispose therein one of the metal terminals and has a sectional shape identical to a sectional shape of the signal-wire connection portion of the metal terminal, the sectional shapes being taken perpendicularly to a direction of insertion of the metal terminal.

3. The gas sensor according to claim 1, wherein the rear insulation member has at least one terminal disposition hole formed so as to dispose therein a plurality of the metal terminals.

4. The gas sensor according to claim 1, wherein the inter-terminal ventilation path is formed in the form of a space extending to all the metal terminals.

5. The gas sensor according to claim 1, wherein
each of the metal terminals comprises a forward terminal member having the element contact portion, and a rear terminal member having the signal-wire connection portion;
the forward terminal member has a female connection portion;
the rear terminal member has a male connection portion connected to the female connection portion; and
the forward terminal member and the rear terminal member electrically connect the corresponding electrode terminal portion and the corresponding signal wire as a result of the male connection portion and the female connection portion being connected together.

6. The gas sensor according to claim 5, wherein the metal terminal has a weld zone for joining the forward terminal member and the rear terminal member together.

7. The gas sensor according to claim 1, wherein the rear insulation member has a ventilation through hole extending therethrough between forward end side and rear end side of the rear insulation member.

* * * * *